United States Patent
Angell et al.

(10) Patent No.: US 7,183,297 B2
(45) Date of Patent: Feb. 27, 2007

(54) BIPHENYL-DERIVATIVES AS P38-KINASE INHIBITORS

(75) Inventors: Richard Martyn Angell, London (GB); Nicola Mary Aston, Stevenage (GB); Paul Bamborough, Stevenage (GB); Mark James Bamford, Harlow (GB); George Stuart Cockerill, London (GB); Stephen Sean Flack, London (GB); Dramane Ibrahim Lainé, Stevenage (GB); Ann Louise Walker, Stevenage (GB)

(73) Assignee: Glaxo Group Limited, Greenford (GB)

(*) Notice: Subject to any disclaimer, the term of this patent is extended or adjusted under 35 U.S.C. 154(b) by 0 days.

(21) Appl. No.: 10/492,715

(22) PCT Filed: Oct. 16, 2002

(86) PCT No.: PCT/EP02/11571
§ 371 (c)(1), (2), (4) Date: Apr. 15, 2004

(87) PCT Pub. No.: WO03/033457
PCT Pub. Date: Apr. 24, 2003

(65) Prior Publication Data
US 2004/0249161 A1 Dec. 9, 2004

(30) Foreign Application Priority Data
Oct. 17, 2001 (GB) ................. 0124934.1

(51) Int. Cl.
*A61K 31/44* (2006.01)
*A61K 31/42* (2006.01)
*C07D 401/00* (2006.01)
*C07D 261/02* (2006.01)
*C07D 333/22* (2006.01)

(52) U.S. Cl. ............. 514/343; 514/378; 514/408; 514/438; 514/461; 546/276.4; 548/240; 549/70; 549/497

(58) Field of Classification Search ............. 546/276.4; 514/277, 613, 343, 378, 408, 438, 461; 564/161; 548/240; 549/70, 497
See application file for complete search history.

(56) References Cited

U.S. PATENT DOCUMENTS

| 4,200,750 | A | 4/1980 | Warner et al. | |
|---|---|---|---|---|
| 4,968,804 | A | 11/1990 | Stanek et al. | 546/257 |
| 5,064,832 | A | 11/1991 | Stanek et al. | 514/256 |
| 5,236,934 | A | 8/1993 | VanAtten | |
| 5,246,943 | A | 9/1993 | Blankley et al. | |
| 5,521,213 | A | 5/1996 | Prasit et al. | |
| 5,534,518 | A | 7/1996 | Henrie et al. | |
| 5,658,903 | A | 8/1997 | Adams et al. | |
| 5,858,995 | A | 1/1999 | Kawai et al. | |
| 5,877,190 | A | 3/1999 | Dhainaut et al. | 514/337 |
| 5,932,576 | A | 8/1999 | Anantanarayan et al. | |
| 5,945,418 | A | 8/1999 | Bemis et al. | |
| 5,977,103 | A | 11/1999 | Adams et al. | |
| 6,060,491 | A | 5/2000 | Pruitt et al. | 514/355 |
| 6,080,767 | A * | 6/2000 | Klein et al. | 514/357 |
| 6,087,496 | A | 7/2000 | Anantanarayan et al. | |
| 6,130,235 | A | 10/2000 | Mavunkel et al. | |
| 6,147,080 | A | 11/2000 | Bemis et al. | |
| 6,174,887 | B1 | 1/2001 | Haruta et al. | |
| 6,251,914 | B1 | 6/2001 | Adams et al. | |
| 6,277,989 | B1 | 8/2001 | Chakravarty et al. | |
| 6,323,227 | B1 * | 11/2001 | Klein et al. | 514/357 |

(Continued)

FOREIGN PATENT DOCUMENTS

EP 0 533 268 9/1992

(Continued)

OTHER PUBLICATIONS

Marin et al., The p38 mitogen-activated protein kinase pathway plays a critical role in thrombin-induced endothelial chemokine production and leukocyte recruitment, Aug. 1, 2001, Blood, vol. 98, No. 3, pp. 667-673, especially p. 667.*

(Continued)

*Primary Examiner*—Joseph K. McKane
*Assistant Examiner*—Susannah L. Chung
(74) *Attorney, Agent, or Firm*—Dara L. Dinner; Stephen Venetianer; Charles M. Kinzig

(57) ABSTRACT

Compounds of formula (I):

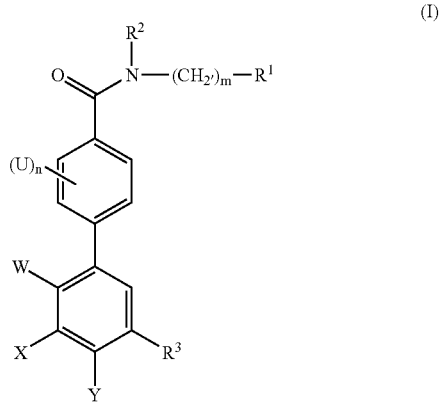

or pharmaceutically acceptable salts or solvates thereof, and their use as pharmaceuticals, particularly as p38 kinase inhibitors.

21 Claims, No Drawings

U.S. PATENT DOCUMENTS

| | | | |
|---|---|---|---|
| 6,392,047 B1 | 5/2002 | Geissler et al. | 546/260 |
| 6,399,627 B1 | 6/2002 | Song et al. | 514/307 |
| 6,420,561 B1 | 7/2002 | Haruta et al. | 544/399 |
| 6,436,925 B1 | 8/2002 | Lubisch et al. | |
| 6,448,257 B1 | 9/2002 | Mavunkel et al. | 514/292 |
| 6,451,794 B1 | 9/2002 | Beswick et al. | |
| 6,498,166 B1 | 12/2002 | Campbell et al. | |
| 6,509,361 B1 | 1/2003 | Weier et al. | |
| 6,509,363 B2 | 1/2003 | Salituro et al. | |
| 6,545,054 B1 | 4/2003 | Song et al. | 514/603 |
| 6,576,632 B1 | 6/2003 | Goldstein et al. | 514/242 |
| 6,579,872 B1 | 6/2003 | Brown et al. | 514/235.5 |
| 6,605,625 B2 | 8/2003 | Peukert et al. | 514/333 |
| 6,638,980 B1 | 10/2003 | Su et al. | |
| 6,696,464 B2 | 2/2004 | McClure et al. | 514/303 |
| 6,699,994 B1 | 3/2004 | Babu et al. | 546/306 |
| 6,774,127 B2 | 8/2004 | Adams et al. | |
| 6,794,377 B2 | 9/2004 | Peukert et al. | 514/183 |
| 6,821,965 B1 | 11/2004 | Brown et al. | 514/217.05 |
| 6,855,719 B1 | 2/2005 | Thomas et al. | |
| 6,867,209 B1 | 3/2005 | Mavunkel et al. | 524/253 |
| 6,924,392 B2 | 8/2005 | Peukert et al. | 564/155 |
| 6,936,719 B2 | 8/2005 | Babu et al. | 546/323 |
| 6,956,037 B2 | 10/2005 | Brown et al. | 514/235.5 |
| 2001/0011135 A1 | 8/2001 | Reidl et al. | |
| 2003/0055088 A1 | 3/2003 | Shao et al. | 514/340 |
| 2003/0139605 A1 | 7/2003 | Riedl et al. | 546/291 |
| 2003/0225089 A1 | 12/2003 | Jung et al. | 514/242 |
| 2004/0038858 A1 | 2/2004 | Dorsch et al. | |
| 2004/0053942 A1 | 3/2004 | Alberti et al. | 514/256 |
| 2004/0116479 A1 | 6/2004 | Haviv et al. | 514/356 |
| 2004/0128287 A1 | 7/2004 | Barth et al. | 514/419 |
| 2004/0162281 A1 | 8/2004 | Babu et al. | 514/217.03 |
| 2004/0176446 A1 | 9/2004 | Alonso-Alija et al. | |
| 2004/0242868 A1 | 12/2004 | Angell et al. | |
| 2004/0249161 A1 | 12/2004 | Angell et al. | 546/228 |
| 2004/0254200 A1 | 12/2004 | Davis et al. | 514/260.1 |
| 2004/0266839 A1 | 12/2004 | Angell et al. | 514/364 |
| 2004/0267012 A1 | 12/2004 | Angell et al. | 544/60 |
| 2005/0020540 A1 | 1/2005 | Angell et al. | 514/63 |
| 2005/0020590 A1 | 1/2005 | Lang et al. | 514/230.5 |
| 2005/0038014 A1 | 2/2005 | Angell et al. | 514/217.12 |
| 2005/0065195 A1 | 3/2005 | Angell et al. | 514/364 |
| 2005/0090491 A1 | 4/2005 | Angell et al. | 514/227.8 |
| 2005/0176964 A1 | 8/2005 | Aston et al. | 546/268.1 |

FOREIGN PATENT DOCUMENTS

| | | |
|---|---|---|
| EP | 0 533 266 | 3/1993 |
| EP | 0 346 841 | 6/2003 |
| EP | 0 430 033 | 4/2004 |
| GB | 2 276 161 | 3/1993 |
| GB | 2 273 930 | 12/1993 |
| GB | 2 276 162 | 9/1994 |
| GB | 2 295 387 | 5/1996 |
| JP | 11218884 | 8/1999 |
| WO | WO 94/15920 | 7/1994 |
| WO | WO 95/06636 | 3/1995 |
| WO | WO 95/06644 | 3/1995 |
| WO | WO 95/11243 | 4/1995 |
| WO | WO 95/15954 | 6/1995 |
| WO | WO 95/17401 | 6/1995 |
| WO | WO 95/29907 | 11/1995 |
| WO | WO 95/30675 | 11/1995 |
| WO | WO 96/31508 | 10/1996 |
| WO | WO 96/31509 | 10/1996 |
| WO | WO 97/03034 | 1/1997 |
| WO | WO 98/57934 | 12/1998 |
| WO | WO 99/32463 | 7/1999 |
| WO | 99/59959 | 11/1999 |
| WO | 00/17175 | 3/2000 |
| WO | WO 00/12074 | 3/2000 |
| WO | WO 00/12497 | 3/2000 |
| WO | WO 00/26216 | 5/2000 |
| WO | WO 00/56738 | 9/2000 |
| WO | WO 00/71493 | 11/2000 |
| WO | WO 00/71509 | 11/2000 |
| WO | WO 00/71510 | 11/2000 |
| WO | WO 00/71511 | 11/2000 |
| WO | WO 01/27089 | 4/2001 |
| WO | WO 01/34605 | 5/2001 |
| WO | WO 01/70695 | 9/2001 |
| WO | WO 01/87875 | 11/2001 |
| WO | WO 02/40486 | 5/2002 |
| WO | WO 03/032970 | 4/2003 |
| WO | WO 03/068747 | 8/2003 |
| WO | WO 03/093248 | 11/2003 |
| WO | WO 04/010995 | 2/2004 |
| WO | WO 04/089874 | 10/2004 |
| WO | WO 04/089875 | 10/2004 |
| WO | WO 04/089876 | 10/2004 |
| WO | WO 05/014550 | 2/2005 |
| WO | WO 05/073189 | 8/2005 |
| WO | WO 05/073217 | 8/2005 |
| WO | WO 05/073219 | 8/2005 |
| WO | WO 05/073232 | 8/2005 |

OTHER PUBLICATIONS

Co-pending U.S. Appl. No. 10/492,605.*
Dhar et al., A Survey of Cyclic Replacements for the Central Diamide Moiety of Inhibitors of Inosine Monophosphate Dehydrogenase, Bio. & Med. Chem. Lett., vol. 12 (2002), pp. 3125-3128, especially p. 3125.*
Boehm et al., Expert Opinion of Therapeutic Patents, vol. 10 (1) pp. 25-37 (2000).
Boehm, et al., Journal of Medicinal Chemistry, vol. 39(20) pp. 3929-3937 (1996).
Ceccarelli et al., European Journal of Medicinal Chemistry, vol. 33 (12) pp. 943-955 (1998).
Gabriele et al., European Journal of Organic Chemistry, vol. 2001 (24) pp. 4607-4613 (2001).
Han et al., Biohemica et Biophysica Acta—Molecular Cell Research, vol. 1265 (2-3) pp. 224-227 (1995.
Hanson, Expert Opinion on Therapeutic Patents, vol. 7(7) pp. 729-733 (1997).
Henry et al., Drugs of the Future, vol. 24 (12) pp. 1345-1354 (1999).
Jiang et al, Journal of Biological Chemistry, vol. 271 (30) pp. 17920-17926 (1996).
Li et al., Biochemical and Biophysical Research Communications, vol. 228 (2) pp. 334-340 (1996).
Liebeskind et al., Organic Letters, vol. 4 (6) pp. 979-981 (2002).
Moreland et al., Annals of Internal Medicine, vol. 130 (6) pp. 478-486 (1999).
Murali Dhar et al., Bioorganic and Medicinal Chemistry Letters, vol. 12 (21) pp. 3125-3128 (2002).
Rankin et al., British Journal of Rheumatology, vol. 34 pp. 334-342 (1995).
Salituro et al., Current Medicinal Chemistry, vol. 6 pp. 807-823 (1999).
Wang et al., Journal of Biological Chemistry, vol. 272 (38) pp. 23668-23674 (1997).
Foster, et al., Drug News Perspect., vol. 13(8) pp. 488-497 (2000).
U.S. Appl. No. 10/513,095, filed Aug. 26, 2005, Angell et al.
U.S. Appl. No. 10/492,714, filed Apr. 15, 2004, Angell et al.
U.S. Appl. No. 10/568,121, filed Feb. 9, 2006, Walker, A.
U.S. Appl. No. 10/522,955, filed Nov. 11, 2005, Angell et al.
U.S. Appl. No. 10/551,503, filed Sep. 30, 2005, Aston, N.
U.S. Appl. No. 10/551,501, filed Sep. 30, 2005, Aston, N.
U.S. Appl. No. 10/551,502, filed Sep. 30, 2005, Aston, et al.
Boehm, et al., Expert Opinion on Therapeutic Patents, vol. 10(1), pp. 25-37 (2000).
Courtney, S. et al., Bioorganic & Medicinal Chemistry Letters, vol. 14 pp. 3269-3273 (2004).

Foster, et al., *Drug News Perspect.*, vol. 13(8) pp. 488-497 (2000).

Hanson, G., Expert Opinion on Therapeutic Patents, vol. 7(7) pp. 729-733 (1997).

Henry, et al., *Bioorganic & Medicinal Chemistry Letters*, vol. 8 pp. 3335-3340 (1998).

Herlaar, et al., Molecular Medicine Today, vol. 5 pp. 439-447 (1999).

Marin, et al., *Blood*, vol. 98(3) pp. 667-673 (2001).

Underwood, et al., *Journal of Pharmacology and Experimental Therapeutics*, vol. 293 (1) pp. 281-288 (2000).

Wadsworth, et al., Journal of Pharmacology and Experimental Therapeutics, vol. 291(2) pp. 680-687 (1999).

* cited by examiner

BIPHENYL-DERIVATIVES AS P38-KINASE INHIBITORS

This application is filed pursuant to 35 U.S.C. §371 as a United States National Phase Application of International Application No. PCT/EP02/11571 filed Oct. 16, 2002, which claims priority from GB 0124934.1 filed Oct. 17, 2001.

This invention relates to novel compounds and their use as pharmaceuticals, particularly as p38 kinase inhibitors, for the treatment of certain diseases and conditions.

We have now found a group of novel compounds that are inhibitors of p38 kinase.

According to the invention there is provided a compound of formula (I):

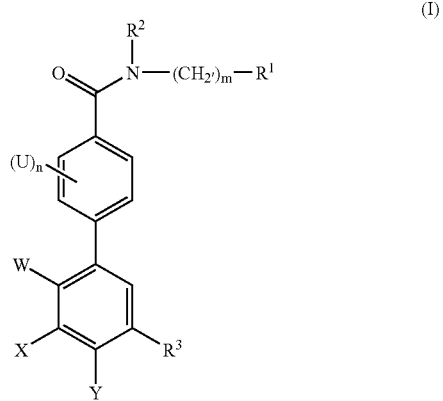

(I)

wherein
$R^1$ is a phenyl group which may be optionally substituted;
$R^2$ is selected from hydrogen, $C_{1-6}$alkyl and $-(CH_2)_q-C_{3-7}$cycloalkyl;
$R^3$ is the group $-NH-CO-R^4$;
$R^4$ is selected from hydrogen, $C_{1-6}$alkyl, $C_{1-6}$alkoxy, $-(CH_2)_q-C_{3-7}$cycloalkyl, trifluoromethyl, $-(CH_2)_r$phenyl optionally substituted by $R^5$ and/or $R^6$, $-(CH_2)_r$heteroaryl optionally substituted by $R^5$ and/or $R^6$, $-(CH_2)_r$heterocyclyl optionally substituted by $R^5$ and/or $R^6$ and $-(CH_2)_r$fused bicyclyl optionally substituted by $R^5$ and/or $R^6$;
$R^5$ is selected from $C_{1-6}$alkyl, $C_{1-6}$alkoxy, $-(CH_2)_q-C_{3-7}$cycloalkyl, $-CONR^7R^8$, $-NHCOR^8$, $-SO_2NHR^7$, $-NHSO_2R^8$, halogen, $-(CH_2)_sNR^9R^{10}$, oxy, trifluoromethyl, phenyl optionally substituted by one or more $R^8$ groups and heteroaryl wherein the heteroaryl may be optionally substituted by one or more $R^6$ groups;
$R^6$ is selected from $C_{1-8}$alkyl, $C_{1-6}$alkoxy, halogen, trifluoromethyl and $-NR^9R^{10}$;
or $R^5$ and $R^6$, together with the carbon atoms to which they are bound, form a five- or six-membered saturated or unsaturated ring to give a fused bicyclic ring system, wherein the ring that is formed by $R^5$ and $R^6$ may optionally contain one or two heteroatoms selected from oxygen, nitrogen and sulfur;
$R^7$ is selected from hydrogen, $C_{1-6}$alkyl and phenyl wherein the phenyl group may be optionally substituted by one or more $R^6$ groups;
$R^8$ is selected from hydrogen and $C_{1-6}$alkyl;
or $R^7$ and $R^8$, together with the nitrogen atom to which they are bound, form a five- to six-membered heterocyclic ring optionally containing one additional heteroatom selected from oxygen, sulfur and $N-R^x$, wherein the ring may be substituted by up to two $C_{1-6}$alkyl groups;
$R^x$ is selected from hydrogen and methyl;
$R^9$ is selected from hydrogen, $C_{1-6}$alkyl and $-(CH_2)_q-C_{3-7}$cycloalkly optionally substituted by $C_{1-6}$alkyl;
$R^{10}$ is selected from hydrogen and $C_{1-6}$alkyl;
or $R^9$ and $R^{10}$, together with the nitrogen atom to which they are bound, form a three- to seven-membered heterocyclic ring optionally containing one additional heteroatom selected from oxygen, sulfur and $N-R^x$, wherein the ring may contain up to one double bond and the ring may be substituted by one or more $R^{11}$ groups;
$R^{11}$ is selected from $C_{1-6}$alkyl, oxy, $-CH_2OC_{1-6}$alkyl, trichloromethyl and $-N(C_{1-6}$alkyl$)_2$;
U is selected from methyl and halogen;
W is selected from methyl and chlorine;
X and Y are each selected independently from hydrogen, methyl and halogen;
m is selected from 0, 1, 2, 3 and 4, and may be optionally substituted with up to two groups selected independently from $C_{1-6}$alkyl;
n is selected from 0, 1 and 2;
q is selected from 0, 1 and 2;
r is selected from 0 and 1;
s is selected from 0, 1, 2 and 3;
or a pharmaceutically acceptable salt or solvate thereof.

According to a further embodiment of the invention there is provided a compound of formula (IA):

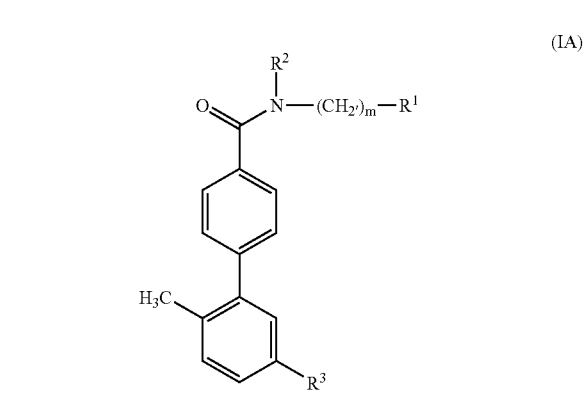

(IA)

wherein
$R^1$, $R^2$, $R^3$ and m are as defined above, or a pharmaceutically acceptable salt or solvate thereof.

In a preferred embodiment, the molecular weight of a compound of formula (I) does not exceed 1000, more preferably 800, even more preferably 600.

The group $R^1$ may be optionally substituted by up to three substituents, more preferably one or two substituents, selected independently from the group consisting of halogen, $C_{1-6}$alkyl, $C_{1-6}$alkoxy, trifluoromethyl, benzyloxy, hydroxy, cyano, hydroxy$C_{1-6}$alkyl, $-(CH_2)_pCO(CH_2)_tNR^{10}R^{11}$, $-(CH_2)_pCO_2R^{10}$, $-(CH_2)_pNR^{10}COR^{11}$, $-(CH_2)_pOCOR^{10}$, $-(CH_2)_pOCONR^{10}R^{11}$, $-(CH_2)_pNR^{10}COOR^{11}$, $-(CH_2)_pCOR^{10}$, $-(CH_2)_pSO_2NR^{10}R^{11}$, $-(CH_2)_pNR^{10}SO_2R^{11}$, $-SO_2R^{10}$, $-(CH_2)_pNR^{10}R^{11}$, $-O(CH_2)_pNR^{10}R^{11}$, $-(CH_2)_pNR^{10}CO(CH_2)_tNR^{10}R^{11}$, $-(CH_2)_pCONR^{10}SO_2R^{11}$, $-(CH_2)_pSO_2NR^{10}COR^{11}$ and phenyloxy optionally substituted by a group A; or $R^1$ may be optionally substituted by two adjacent substituents which, together with the carbon atoms to which they are bound, form a five- or six-membered saturated or unsaturated ring to give a fused bicyclic ring system. The ring that is fused to the phenyl ring may optionally contain one or two heteroatoms selected from oxygen, nitrogen and sulfur. The group $R^1$ may also be optionally substituted by three, more preferably one or two, $C_{3-7}$cycloalkyl groups.

$R^{10}$ and $R^{11}$ are independently selected from hydrogen, $C_{1-6}$alkyl, trihalomethyl, benzyl, —$(CH_2)_v$OH, —$(CH_2)_v$NR$^{12}$R$^{13}$ and phenyl optionally substituted by up to three groups selected from $C_{1-6}$alkyl and $C_{1-6}$alkoxy.

$R^{12}$ and $R^{13}$ are independently selected from hydrogen and $C_{1-4}$alkyl.

A is selected from halogen, —SO$_2$NH$_2$, —SO$_2$-(4-methyl)piperazinyl, —NR$^{10}$COC$_{1-6}$alkyl and —NR$^{10}$SO$_2$C$_{1-6}$alkyl.

p is selected from 0, 1, 2 and 3.
t is selected from 0, 1, 2 and 3.
v is selected from 2 and 3.

The optional substituents on the group $R^1$, including when the phenyl ring is part of a fused bicyclic system, may be located on any position on the phenyl ring. In a more preferred embodiment, when there is one substituent on the group $R^1$, that substituent is located on the meta- or para-position relative to the amide linkage. When there are two optional substituents on the group $R^1$, these substituents preferably occupy the meta- and para-positions relative to the amide linkage.

Preferred subtituents for the group $R^1$ are halogen, $C_{1-4}$alkyl, trifluromethyl, $C_{1-4}$alkoxy, phenyloxy optionally substituted by the group A, benzyloxy, hydroxy, cynao, —CH$_2$CH$_2$OH, —(CH$_2$)$_p$-NHCH$_3$, —(CH$_2$)$_p$-N(CH$_3$)$_2$, —(CH$_2$)$_p$CONR$^{10}$R$^{11}$, —(CH$_2$)$_p$CO$_2$R$^{10}$, —(CH$_2$)$_p$NR$^{10}$COR$^{11}$, —(CH$_2$)$_p$OCOR$^{10}$, —(CH$_2$)$_p$OCONR$^{10}$R$^{11}$, —(CH$_2$)$_p$NR$^{10}$COOR$^{11}$, —(CH$_2$)$_p$COR$^{10}$, —(CH$_2$)$_p$SO$_2$NR$^{10}$R$^{11}$, —(CH$_2$)$_p$NR$^{10}$SO$_2$R$^{11}$, —SO$_2$R$^{10}$, —(CH$_2$)$_p$NR$^{10}$R$^{11}$, —(CH$_2$)$_p$NR$^{10}$CONR$^{10}$R$^{11}$ and —(CH$_2$)$_p$CONR$^{10}$SO$_2$R$^{11}$. In a particularly preferred embodiment, substituents for the group $R^1$ are selected from $C_{1-4}$alkoxy, in particular methoxy; hydroxy; —(CH$_2$)$_p$NR$^{10}$SO$_2$R$^{11}$, in particular —NHSO$_2$CH$_3$ or —CH$_2$NHSO$_2$CH$_3$; and —(CH$_2$)$_p$NR$^{10}$R$^{11}$, in particular —CH$_2$N(CH$_3$)$_2$. In a preferred embodiment, $R^2$ is selected from hydrogen, $C_{1-4}$alkyl and —CH$_2$-cyclopropyl, more preferably hydrogen.

In a preferred embodiment, $R^4$ is selected from —(CH$_2$)$_r$phenyl optionally substituted by $R^5$ and/or $R^6$ and —(CH$_2$)$_r$heteroaryl optionally substituted by $R^5$ and/or $R^6$. In a particularly preferred embodiment, $R^4$ is —(CH$_2$)$_r$heteroaryl optionally substituted by $R^5$ and/or $R^6$, especially furyl, thienyl, isoxazolyl or pyridyl optionally substituted by —(CH$_2$)$_s$NR$^9$R$^{10}$.

In a preferred embodiment, $R^5$ is selected from $C_{1-4}$alkyl, halogen, —NR$^9$R$^{10}$, $C_{3-6}$cycloalkyl, phenyl optionally substituted by one or more $R^6$ groups and heteroaryl optionally substituted by one or more $R^6$ groups.

In a preferred embodiment, $R^6$ is selected from $C_{1-2}$alkyl and halogen. In a further preferred embodiment, $R^6$ is —NR$^9$R$^{10}$.

In a preferred embodiment, $R^7$ is selected from hydrogen and $C_{1-4}$alkyl.

In a preferred embodiment, $R^8$ is selected from hydrogen and $C_{1-4}$alkyl.

In a preferred embodiment, $R^9$ is selected from hydrogen, $C_{1-4}$alkyl, $C_{3-6}$cycloalkyl and —CH$_2$C$_{3-6}$cycloalkyl.

In a preferred embodiment, $R^{10}$ is selected from hydrogen and $C_{1-4}$alkyl.

In a preferred embodiment, $R^9$ and $R^{10}$, together with the nitrogen atom to which they are bound, form a five to six membered heterocyclic ring optionally containing up to one additional heteroatom selected from oxygen, sulfur and N—R$^x$, wherein R$^x$ is methyl, and the ring may be substituted by one or more $R^{11}$ groups. In a further preferred embodiment, $R^9$ and $R^{10}$, together with the nitrogen atom to which they are bound, form a pyrrolidinyl group.

In a preferred embodiment, $R^{11}$ is selected from methyl and oxy.

In a preferred embodiment, W is methyl.

In a preferred embodiment, X and Y are each selected independently from hydrogen, chlorine and fluorine. In a further preferred embodiment, X is fluorine.

In a preferred embodiment, m is selected from 0, 1 and 2.

In a preferred embodiment, n is selected from 0 and 1. In particular, n is 0.

In a preferred embodiment, p, s and t are independently selected from 0, 1 and 2.

In a preferred embodiment, q and r are independently 0.

It is to be understood that the present invention covers all combinations of particular and preferred groups described hereinabove.

Particular compounds according to the invention include those mentioned in the examples and their pharmaceutically acceptable salts and solvates. Specific examples which may be mentioned include:

N-(4'-{[(3-Methoxybenxyl)amino]carbonyl}-6-methyl-1,1'-biphenyl-3-yl)-2-pyrrolidin-1-ylisonicotinamide; and N-{4'-[(4-Methoxyanilino)carbonyl]-6-methyl-1,1'-biphenyl-3-yl}-2-pyrrolidin-1-ylisonicotinamide.

Further specific examples which may be mentioned include:

N-(4'-{[(2-Hydroxybenzyl)amino]carbonyl}-6-methyl-1,1'-biphenyl-3-yl)thiophene-3-carboxamide;

N-(4'-{[(4-Hydroxybenzyl)amino]carbonyl}-6-methyl-1,1'-biphenyl-3-yl)thiophene-3-carboxamide;

N-(4'-{[(3-Hydroxybenzyl)amino]carbonyl}-6-methyl-1,1'-biphenyl-3-yl)thiophene-3-carbonamide;

N-(4'-{[(3,5-Dihydroxybenzyl)amino]carbonyl}-6-methyl-1,1'-biphenyl-3-yl)thiophene-3-carboxamide;

N-(4'-{[(3-Methoxybenzyl)amino]carbonyl}-6-methyl-1,1'-biphenyl-3-yl)isoxazole-5-carboxamide;

N-{6-Methyl-4'-[({4-[(methylsulfonyl)amino]phenyl}amino)-carbonyl]-1,1'-biphenyl-3-yl}isoxazole-5-carboxamide;

N-(6-Methyl-4'-{[(4-{[(methylsulfonyl)amino]methyl}phenyl)-amino]-carbonyl}-1,1'-biphenyl-3-yl)isoxazole-5-carboxamide;

N-(4'-{[(3-Methoxybenzyl)amino]carbonyl}-6-methyl-1,1'-biphenyl-3-yl)thiophene-3-carboxamide;

N-{6-Methyl-4'-[({4-[(methylsulfonyl)amino]phenyl}amino)carbonyl]-1,1'-biphenyl-3-yl}thiophene-3-carboxamide;

N-{4'-[({3-[(Dimethylamino)methyl]benzyl}amino)carbonyl]-6-methyl-1,1'-biphenyl-3-yl}thiophene-3-carboxamide;

N-(4'-{[(3,5-Dihydroxybenzyl)amino]carbonyl}-6-methyl-1,1'-biphenyl-3-yl)-3-furamide;

N-(4'-{[(2-Hydroxybenzyl)amino]carbonyl}-6-methyl-1,1'-biphenyl-3-yl)-3-furamide;

N-(4'-{[(3-Hydroxybenzyl)amino]carbonyl}-6-methyl-1,1'-biphenyl-3-yl)-3-furamide;

N-(6-Methyl-4'-{[(4-{[(methylsulfonyl)amino]methyl}phenyl)amino]-carbonyl}-1,1'-biphenyl-3-yl)-3-furamide; and N-{6-Methyl-4'-[({4-[(methylsulfonyl)amino]phenyl}amino)carbonyl]-1,1'-biphenyl-3-yl}-3-furamide.

As used herein, the term "alkyl" refers to straight or branched hydrocarbon chains containing the specified number of carbon atoms. For example, $C_{1-6}$alkyl means a straight or branched alkyl containing at least 1, and at most 6, carbon atoms. Examples of "alkyl" as used herein include, but are not limited to, methyl, ethyl, n-propyl, n-butyl, n-pentyl, isobutyl, isopropyl and t-butyl. A $C_{1-4}$alkyl group is preferred, for example methyl, ethyl or isopropyl. The said alkyl group may be optionally substituted with one or more fluorine atoms, for example, trifluoromethyl.

As used herein, the term "alkoxy" refers to a straight or branched chain alkoxy group, for example, methoxy, ethoxy, propoxy, prop-2-oxy, butoxy, but-2-oxy, 2-methylprop-1-oxy, 2-methylprop-2-oxy, pentoxy, or hexyloxy. A $C_{1-4}$alkoxy group is preferred, for example methoxy or ethoxy.

As used herein, the term "cycloalkyl" refers to a non-aromatic hydrocarbon ring containing the specified number of carbon atoms. For example, $C_{3-7}$cycloalkyl means a non-aromatic ring containing at least three, and at most seven, ring carbon atoms. Examples of "cycloalkyl" as used herein include, but are not limited to, cyclopropyl, cyclobutyl, cyclopentyl, cyclohexyl and cycloheptyl. A $C_{3-5}$ cycloalkyl group is preferred, for example cyclopropyl.

As used herein, the terms "heteroaryl ring" and "heteroaryl" refer to a monocyclic five- to seven-membered unsaturated hydrocarboned ring containing at least one heteroatom independently selected from oxygen, nitrogen and sulfur. Preferably, the heteroaryl ring has five or six ring atoms. Examples of heteroaryl rings include, but are not limited to, furyl, thienyl, pyrrolyl, oxazolyl, thiazolyl, isoxazolyl, isothiazolyl, imidazolyl, pyrazolyl, oxadiazolyl, triazolyl, tetrazolyl, thiadiazolyl, pyridyl, pyridazinyl, pyrimidinyl, pyrazinyl, and triazinyl. A particularly preferred heteroaryl ring is pyridyl. The said ring may be optionally substituted by one or more substituents independently selected from $C_{1-6}$alkyl and oxy.

As used herein, the terms "heterocyclic ring" and "heterocyclyl" refer to a monocyclic three- to seven-membered saturated or non-aromatic, unsaturated hydrocarbon ring containing at least one heteroatom independently selected from oxygen, nitrogen and sulfur. Preferably, the heterocyclyl ring has five or six ring atoms. Examples of heterocyclyl groups include, but are not limited to, aziridinyl, pyrrolinyl, pyrrolidinyl, imidazolinyl, imidazolidinyl, pyrazolinyl, pyrazolidinyl, piperidyl, piperazinyl, morpholino, and thiomorpholino. The said ring may be optionally substituted by one or more substituents independently selected from $C_{1-6}$alkyl and oxy.

As used herein, the terms "fused bicyclic ring system" and "fused bicyclyl" refer to a ring system comprising two five- to seven-membered saturated or unsaturated hydrocarbon rings, the ring system optionally containing one or more heteroatoms independently selected from oxygen, nitrogen and sulfur. Preferably, each ring has five or six ring atoms. Examples of suitable fused bicyclic rings include, but are not limited to, naphthyl, indolyl, indolinyl, benzothienyl, quinolyl, isoquinolyl, tetrahydroquinolyl, benzodioxzanyl, indanyl and tetrahydronaphthyl. Each ring may be optionally substituted with one or more substituents independently selected from halogen, $C_{1-6}$alkyl, oxy, $—(CH_2)_p NR^{10}R^{11}$, $—CO(CH_2)_p NR^{10}R^{11}$, and imidazolyl. Particularly preferred substituents are chlorine, imidazolyl and $—CH_2—N(CH_3)_2$.

As used herein, the terms "halogen" or "halo" refer to the elements fluorine, chlorine, bromine and iodine. Preferred halogens are fluorine, chlorine and bromine. A particularly preferred halogen is fluorine.

As used herein, the term "optionally" means that the subsequently described event(s) may or may not occur, and includes both event(s) which occur and events that do not occur.

As used herein, the term "substituted" refers to substitution with the named substituent or substituents, multiple degrees of substitution being allowed unless otherwise stated.

As used herein, the term "solvate" refers to a complex of variable stoichiometry formed by a solute (in this invention, a compound of formula (I) or a salt thereof) and a solvent. Such solvents for the purpose of the invention may not interfere with the biological activity of the solute. Examples of suitable solvents include water, methanol, ethanol and acetic acid. Preferably the solvent used is a pharmaceutically acceptable solvent. Examples of suitable pharmaceutically acceptable solvents include water, ethanol and acetic acid. Most preferably the solvent used is water.

Certain compounds of formula (I) may exist in stereoisomeric forms (e.g. they may contain one or more asymmetric carbon atoms or may exhibit cis-trans isomerism). The individual stereoisomers (enantiomers and diastereomers) and mixtures of these are included within the scope of the present invention. The present invention also covers the individual isomers of the compounds represented by formula (I) as mixtures with isomers thereof in which one or more chiral centres are inverted. Likewise, it is understood that compounds of formula (I) may exist in tautomeric forms other than that shown in the formula and these are also include within the scope of the present invention.

Salts of the compounds of the present invention are also encompassed within the scope of the invention and may, for example, comprise acid addition salts resulting from reaction of an acid with a nitrogen atom present in a compound of formula (I).

Salts encompassed within the term "pharmaceutically acceptable salts" refer to non-toxic salts of the compounds of this invention. Representative salts include the following salts: Acetate, Benzenesulfonate, Benzoate, Bicarbonate, Bisulfate, Bitartrate, Borate, Bromide, Calcium Edetate, Camsylate, Carbonate, Chloride, Clavulanate, Citrate, Dihydrochloride, Edetate, Edisylate, Estolate, Esylate, Fumarate, Gluceptate, Gluconate, Glutamate, Glycollylarsanilate, Hexylresorcinate, Hydrabamine, Hydrobromide, Hydrochloride, Hydroxynaphthoate, Iodide, Isethionate, Lactate, Lactobionate, Laurate, Malate, Maleate, Mandelate, Mesylate, Methylbromide, Methylnitrate, Methylsulfate, Monopotassium Maleate, Mucate, Napsylate, Nitrate, N-methylglucamine, Oxalate, Pamoate (Embonate), Palmitate, Pantothenate, Phosphate/diphosphate, Polygalacturonate, Potassium, Salicylate, Sodium, Stearate, Subacetate, Succinate, Tannate, Tartrate, Teoclate, Tosylate, Triethiodide, Trimethylammonium and Valerate. Other salts which are not pharmaceutically acceptable may be useful in the preparation of compounds of this invention and these form a further aspect of the invention.

The compounds of this invention may be made by a variety of methods, including standard chemistry. Any previously defined variable will continue to have the previously defined meaning unless otherwise indicated. Illustrative general synthetic methods are set out below and then specific compounds of the invention are prepared in the working Examples.

For example, a general method (A) for preparing the compounds of Formula (I) comprises the reactions set out in Scheme 1 below.

Scheme 1
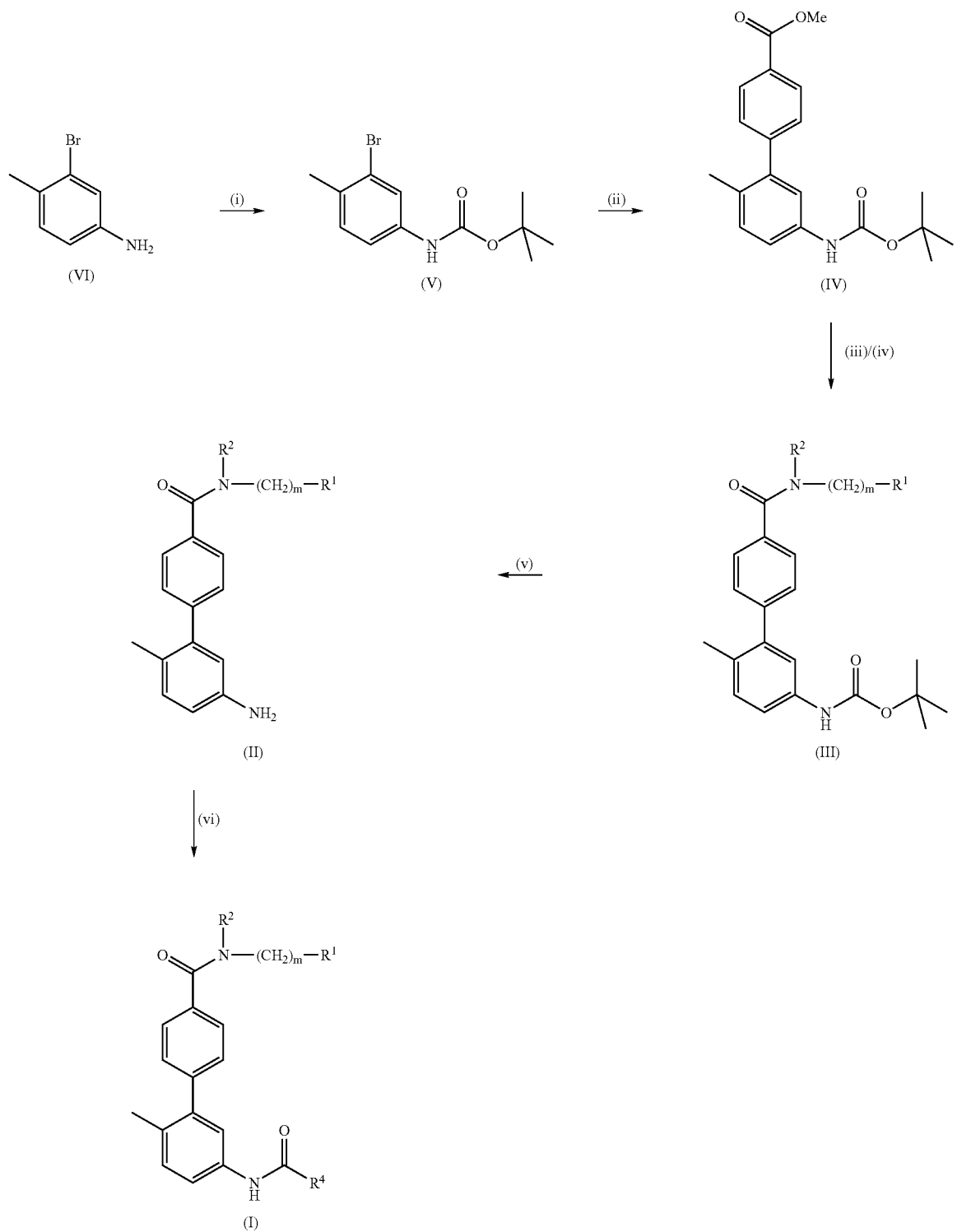
(i) Di-t-butyldicarbonate, Et₃N, DCM
(ii) (4-Methoxycarbonylphenyl)boronic acid, (Ph₃P)₄Pd, CsCO₃, DME
(iii) LiOH, THF, H₂O
(iv) R¹(CH₂)ₘN R²H, HATU, DIPEA, THF
(v) TFA, DCM
(vi) R⁴COOH, HATU, DIPEA, DMF
For example, a general method (B) for preparing the compound of Formula (I) comprises the reactions set out in Scheme 2 below.

Scheme 2
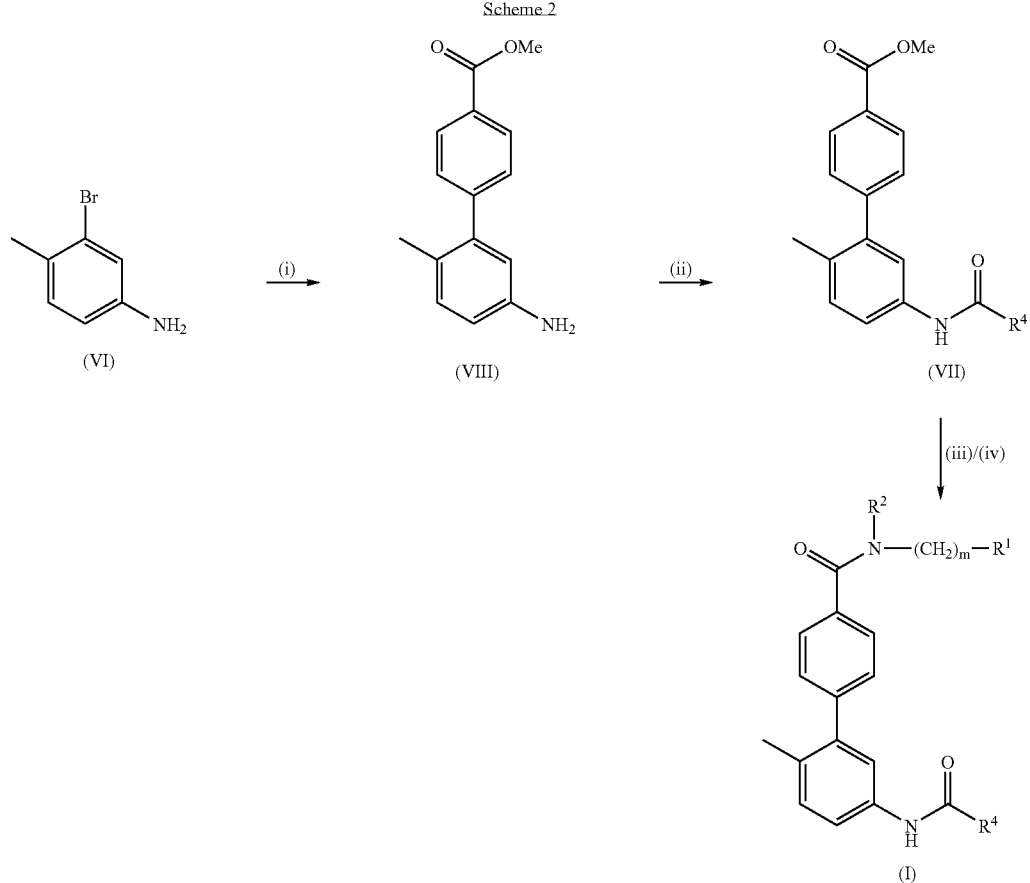
(i) (4-Methoxycarbonylphenyl)boronic acid, $(Ph_3P)_4Pd$, $CsCO_3$, DME
(ii) $R^4COOH$, HATU, DIPEA, DMF
(iii) LiOH, THF, $H_2O$
(iv) $R^1(CH_2)_mN\ R^2H$, HATU, DIPEA, THF
For example, a general method (C) for preparing the compounds of Formula (I) wherein $R^4$ is
comprises the reactions set out in Scheme 3 below.
Scheme 3
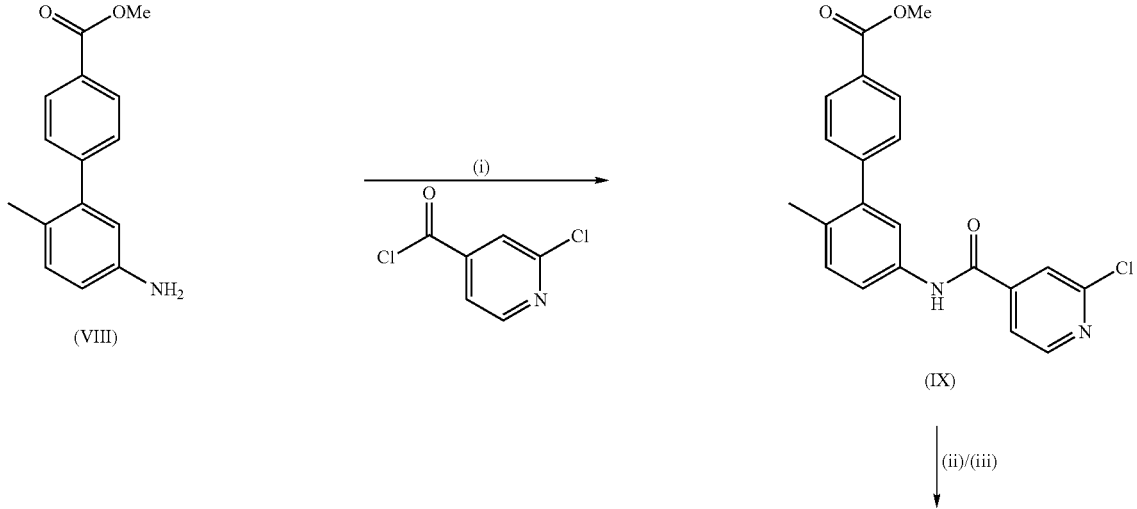

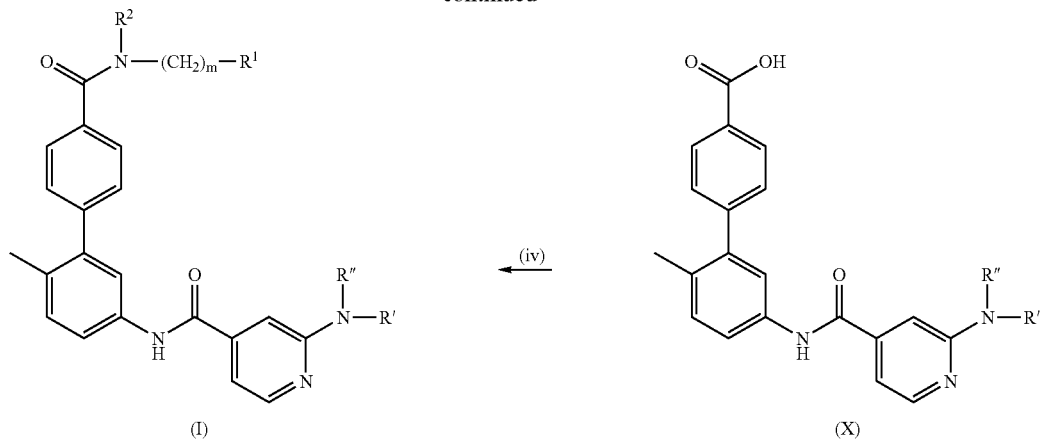
(i) Et₃N, DCM
(ii) LiOH, THF, H₂O
(iii) R'R"NH
(iv) R¹(CH₂)$_m$N R²H, HATU, DIPEA, THF
For example, a general method (D) for preparing the compounds of Formula (I) comprises the reactions set out in Scheme 4 below:
(i) (4-Methoxycarbonylphenyl)boronic acid, (Ph₃P)₄Pd, CsCO₃, DME
(ii) LiOH, THF, H₂O
(iii) R¹(CH₂)$_m$N R²H, HATU, DIPEA, THF
(iv) R⁴COCl, ET₃N, DCM
Scheme 4
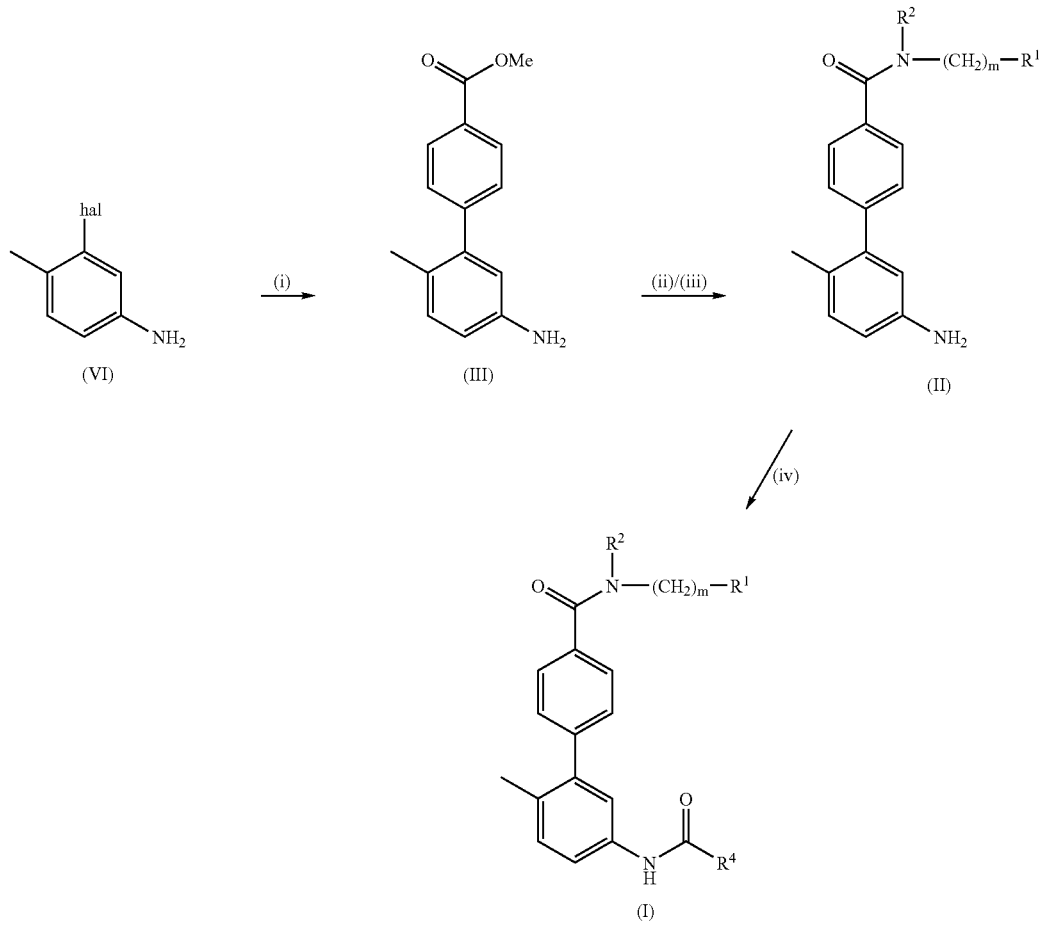

Thus, according to the invention there is provided a process for preparing a compound of formula (I) which comprises:

(a) reacting a compound of formula (IX)

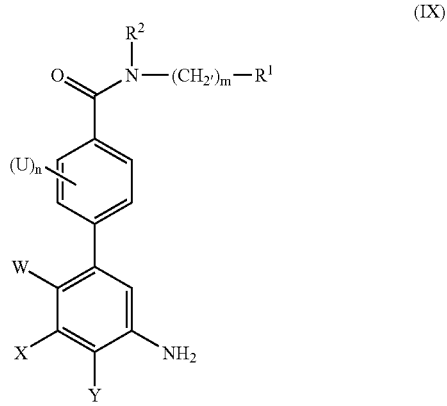

(IX)

wherein $R^1$, $R^2$, U, W, X, Y, m and n are as defined above, with a compound of formula (X)

wherein $R^4$ is as defined above, under amide forming conditions (if desired, the acid compound (X) may be converted to an activated form of the acid, for example the acid chloride, and then the activated acid thus formed reacted with the amine compound (IX)); or (b) reacting a compound of formula (XI)

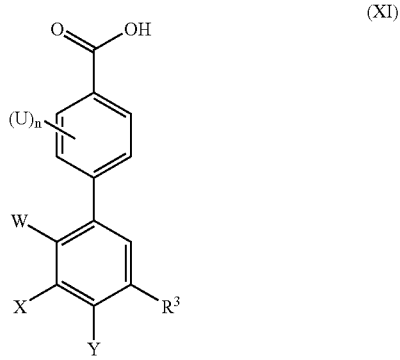

(XI)

wherein $R^3$, U, W, X, Y and n are as defined above, with a compound of formula (XII)

wherein $R^1$, $R^2$ and m are as defined above, under amide forming conditions.

Suitable amide forming conditions are well known in the art and include treating a solution of the acid, in for example THF, with an amine in the presence of, for example, HATU and DIPEA.

Whilst it is possible for the compounds, salts or solvates of the present invention to be administered as the new chemical, the compounds of formula (I) and their pharmaceutically acceptable salts and solvates are conveniently administered in the form of pharmaceutical compositions. Thus, in another aspect of the invention, we provide a pharmaceutical composition comprising a compound of formula (I) or a pharmaceutically acceptable salt or solvate thereof in admixture with one or more pharmaceutically acceptable carriers, diluents or excipients.

The compounds of formula (I) and their pharmaceutically acceptable salts and solvants may be formulated for administration in any suitable manner. They may, for example, be formulated for topical administration or administration by inhalation or, more preferably, for oral, transdermal or parenteral administration. The pharmaceutical composition may be in a form such that it can effect controlled release of the compounds of formula (I) and their pharmaceutically acceptable salts and solvates. A particularly preferred method of administration, and corresponding formulation, is oral administration.

For oral administration, the pharmaceutical composition may take the form of, and be administered as, for example, tablets (including sub-lingual tablets) and capsules (each including timed release and sustained release formulations), pills, powders, granules, elixirs, tinctures, emulsions, solutions, syrups or suspensions prepared by conventional means with acceptable excipients.

For instance, for oral administration in the form of a tablet or capsule, the active drug component can be combined with an oral, non-toxic pharmaceutically acceptable inert carrier such as ethanol, glycerol, water and the like. Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agent can also be present.

Capsules can be made by preparing a powder mixture as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar—agar, calcium carbonate or sodium carbonate can also be added to improve the availability of the medicament when the capsule is ingested.

Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an alginate, gelatin, or polyvinyl pyrrolidone, a solution retardant such as paraffin, a resorption accelerator such as quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additives such as peppermint oil or saccharin, and the like can also be added.

Where appropriate, dosage unit formulations for oral administration can be microencapsulated. The formulation can also be prepared to prolong or sustain the release as for example by coating or embedding particulate material in polymers, wax or the like.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compounds of the present invention can also be administered in the form of liposome emulsion delivery systems, such as small unilamellar vesicles, large unilamellar vesicles and multilamellar vesicles. Liposomes can be formed from a variety of phospholipids, such as cholesterol, stearylamine or phosphatidycholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxidepolyl- ysine substituted with palmitoyl residues. Furthermore, the compounds of the present invention may be coupled to a class of biodegradable polymers useful in achieving controlled release of a drug, for example, polylactic acid, polepsilon, caproactone, polyhydroxy butyric acid, polyorthoesters, polyacetals, polydihydropyrans, polycyanoacrylates and cross-linked or amphipathic block copolymers of hydrogels.

The present invention includes pharmaceutical compositions containing 0.1 to 99.5%, more particularly, 0.5 to 90% of a compound of the formula (I) in combination with a pharmaceutically acceptable carrier.

Likewise, the composition may also be administered in nasal, ophthalmic otic, rectal, topical, intravenous (both bolus and infusion), intraperitoneal, intraarticular, subcutaneous or intramuscular, inhalation or insufflation form, all using forms well known to those of ordinary skill in the pharmaceutical arts.

For transdermal administration, the pharmaceutical composition may be given in the form of a transdermal patch, such as a transdermal iontophoretic patch.

For parenteral administration, the pharmaceutical composition may be given as an injection or a continuous infusion (e.g. intravenously, intravascularly or subcutaneously). The compositions may take such forms as suspensions, solutions or emulsions in oily or aqueous vehicles and may contain formulatory agents such as suspending, stabilizing and/or dispersing agents. For administration by injection these may take the form of a unit dose presentation or as a multidose presentation preferably with an added preservative. Alternatively for parenteral administration the active ingredient may be in powder form for reconstitution with a suitable vehicle.

The compounds of the invention may also be formulated as a depot preparation. Such long acting formulations may be administered by implantation (for example subcutaneously or intramuscularly) or by intramuscular injection. Thus, for example, the compounds of the invention may be formulated with suitable polymeric or hydrophobic materials (for example as an emulsion in an acceptable oil) or ion exchange resins, or as sparingly soluble derivatives, for example, as a sparingly soluble salt.

Alternatively the composition may be formulated for topical application, for example in the form of ointments, creams, lotions, eye ointments, eye drops, ear drops, mouthwash, impregnated dressings and sutures and aerosols, and may contain appropriate conventional additives, including, for example, preservatives, solvents to assist drug penetration, and emollients in ointments and creams. Such topical formulations may also contain compatible conventional carriers, for example cream or ointment bases, and ethanol or oleyl alcohol for lotions. Such carriers may constitute from about 1% to about 98% by weight of the formulation; more usually they will constitute up to about 80% by weight of the formulation.

For administration by inhalation the compounds according to the invention are conveniently delivered in the form of an aerosol spray presentation from pressurized packs or a nebulizer, with the use of a suitable propellant, e.g. dichlorodifluoromethane, trichlorofluoromethane, dichlorotetrafluorethane, tetrafluoroethane, heptafluoropropane, carbon dioxide or other suitable gas. In the case of a pressurized aerosol the dosage unit may be determined by providing a value to deliver a metered amount. Capsules and cartridges of e.g. gelatin for use in an inhaler or insufflator may be formulated containing a powder mix of a compound of the invention and a suitable powder base such as lactose or starch.

The pharmaceutical compositions generally are administered in an amount effective for treatment or prophylaxis of a specific condition or conditions. Initial dosing in human is accomplished by clinical monitoring of symptoms, such symptoms for the selected condition. In general, the compositions are administered in an amount of active agent of at least about 100 µg/kg body weight. In most cases they will be administered in one or more doses in an amount not in excess of about 20 mg/kg body weight per day. Preferably, in most cases, dose is from about 100 µg/kg to about 5 mg/kg body weight, daily. For administration particularly to mammals, and particularly humans, it is expected that the daily dosage level of the active agent will be from 0.1 mg/kg to 10 mg/kg and typically around 1 mg/kg. It will be appreciated that optimum dosage will be determined by standard methods for each treatment modality and indication, taking into account the indication, its severity, route of administration, complicating conditions and the like. The physician in any event will determine the actual dosage which will be most suitable for an individual and will vary with the age, weight and response of the particular individual. The effectiveness of a selected actual dose can readily be determined, for example, by measuring clinical symptoms or standard anti-inflammatory indicia after administration of the selected dose. The above dosages are exemplary of the average case. There can, of course, be individual instances where higher or lower dosage ranges are merited, and such are within the scope of this invention. For conditions or disease states as are treated by the present invention, maintaining consistent daily levels in a subject over an extended period of time, e.g., in a maintenance regime, can be particularly beneficial.

In another aspect, the present invention provides a compound of formula (I) or a salt or solvate thereof, for use in therapy.

The compounds of the present invention are generally inhibitors of the serine/threonine kinase p38 and are therefore also inhibitors of cytokine production which is mediated by p38 kinase. Within the meaning of the term "inhibitors of the serine/threonine kinase p38" are included those compounds that interfere with the ability of p38 to transfer a phosphate group from ATP to a protein substrated according to the assay described below.

It will be appreciated that the compounds of the invention may be selected for one or more of the isoforms of p38, for example p38α, p38β, p38γ and/or p38δ. In one embodiment, the compounds of the invention selectively inhibit the p38α isoform. In another embodiment, the compounds of the invention selectively inhibit the p38β isoform. In a further embodiment, the compounds of the invention selectively inhibit the p38α and p38β isoforms. Assays for determining the selectivity of compounds for the p38 isoforms are described in, for example, WO 99/61426, WO 00/71535 and WO 02/46158.

It is known that p38 kinase activity can be elevated (locally or throughout the body), p38 kinase can be incorrectly temporally active or expressed, p38 kinase can be expressed or active in an inappropriate location, p38 kinase can be constitutively expressed, or p38 kinase expression can be erratic; similarly, cytokine production mediated by p38 kinase activity can be occurring at inappropriate times, inappropriate locations, or it can occur at detrimentally high levels.

Accordingly, the present invention provides a method for the treatment of a condition or disease state mediated by p38 kinase activity, or mediated by cytokines produced by the activity of p38 kinase, in a subject which comprises administering to said subject a therapeutically effective amount of a compound of formula (I) or a pharmaceutically acceptable salt or solvate thereof. The compound may be administered as a single or polymorphic crystalline form or forms, an amorphous form, a single enantiomer, a racemic mixture, a single stereoisomer, a mixture of stereoisomers, a single diasteroisomer or a mixture of diastereoisomers.

The present invention also provides a method of inhibiting cytokine production which is mediated by p38 kinase activity in a subject, e.g. a human which comprises administering to said subject in need of cytokine production inhibition a therapeutic, or cytokine-inhibiting, amount of a compound of the present invention. The compound may be administered as a single or polymorphic crystalline form or forms, an amorphous form, a single enantiomer, a racemic mixture, a single stereoisomer, a mixture of stereoisomers, a single diastereoisomer or a mixture of diasteroisomers.

The present invention treats these conditions by providing a therapeutically effective amount of a compound of this invention. By "therapeutically effective amount" is meant a symptom-alleviating or symptom-reducing amount, a cytokine-reducing amount, a cytokine-inhibiting amount, a kinase-regulating amount and/or a kinase-inhibiting amount of a compound. Such amounts can be readily determined by standard methods, such as by measuring cytokine levels or observing alleviation of clinical symptoms. For example, the clinician can monitor accepted measurement scores for anti-inflammatory treatments.

The compounds of the present invention can be administered to any subject in need of inhibition or regulation of p38 kinase or in need of inhibition or regulation of p38 mediated cytokine production. In particular, the compounds may be administered to mammals. Such mammals can include, for example, horses, cows, sheep, pigs, mice, dogs, cats, primates such as chimpanzees, gorillas, rhesus monkeys, and, most preferably, humans.

Thus, the present invention provides methods of treating or reducing symptoms in a human or animal subject suffering from, for example, rheumatoid arthritis, osteoarthritis, asthma, psoriasis, eczema, allergic rhinitis, allergic conjunctivitis, adult respiratory distress syndrome, chronic pulmonary inflammation, chronic obstructive pulmonary disease, chronic heart failure, silicosis, endotoxemia, toxic shock syndrome, inflammatory bowel disease, tuberculosis, atherosclerosis, neurodegenerative disease, Alzheimer's disease, Parkinson's disease, Huntington's disease, amyotrophic lateral sclerosis, epilepsy, multiple sclerosis, aneurism, stroke, irritable bowel syndrome, muscle degeneration, bone resorption diseases, osteoporosis, diabetes, reperfusion injury, graft vs. host reaction, allograft rejections, sepsis, systemic cachexia, cachexia secondary to infection or malignancy, cachexia secondary to aquired immune deficiency syndrome (AIDS), malaria, leprosy, infectious arthritis, leishmaniasis, Lyme disease, glomerulonephritis, gout, psoriatic arthritis, Reiter's syndrome, traumatic arthritis, rubella arthritis, Crohn's disease, ulcerative colitis, acute synovitis, gouty arthritis, spondylitis, and non articular inflammatory conditions, for example, herniated/ruptured/prolapsed intervertebral disk syndrome, bursitis, tendonitis, tenosynovitis, fibromyalgic syndrome and other inflammatory conditions associated with ligamentous sprain and regional musculoskeletal strain, pain, for example that associated with inflammation and/or trauma, osteopetrosis, restenosis, thrombosis, angiogenesis, cancer including breast cancer, colon cancer, lung cancer or prostatic cancer, which comprises administering to said subject a therapeutically effective amount of a compound of formula (I) or a pharmaceutically acceptable salt or solvate thereof.

A further aspect of the invention provides a method of treatment of a human or animal subject suffering from rheumatoid arthritis, asthma, psoriasis, chronic pulmonary inflammation, chronic obstructive pulmonary disease, chronic heart failure, systemic cachexia, glomerulonephritis, Crohn's disease, neurodegenerative disease, Alzheimer's disease, Parkinson's disease, epilepsy and cancer including breast cancer, colon cancer, lung cancer and prostatic cancer, which comprises administering to said subject a therapeutically effective amount of a compound of formula (I) or a pharmaceutically acceptable salt or solvate thereof.

A further aspect of the invention provides a method of treatment of a human or animal subject suffering from rheumatoid arthritis, asthma, psoriasis, chronic pulmonary inflammation, chronic obstructive pulmonary disease, chronic heart failure, systemic cachexia, glomerulonephritis, Crohn's disease and cancer including breast cancer, colon cancer, lung cancer and prostatic cancer, which comprises administering to said subject a therapeutically effective amount of a compound of formula (I) or a pharmaceutically acceptable salt or solvate thereof.

A further aspect of the invention provides a method of treatment of a human or animal subject suffering from rheumatoid arthritis, neurodegenerative disease, Alzheimer's disease, Parkinson's disease and epilepsy which comprises administering to said subject a therapeutically effective amount of a compound of formula (I) or a pharmaceutically acceptable salt or solvate thereof.

A further aspect of the invention provides a method of treatment of a human or animal subject suffering from any type of pain including chronic pain, rapid onset of analgesis, neuromuscular pain, headache, cancer pain, acute and chronic inflammatory pain associated with osteoarthritis and rheumatoid arthritis, post operative inflammatory pain, neuropathic pain, diabetic neuropathy, trigeminal neuralgia, post-hepatic neuralgia, inflammatory neuropathies and migraine pain which comprises administering to said subject a therapeutically effective amount of a compound of formula (I) or a pharmaceutically acceptable salt or solvant thereof.

A further aspect of the invention provides the use of a compound of formula (I), or a pharmaceutically acceptable salt or solvate thereof, for the preparation of a medicament for the treatment of a condition or disease state mediated by p38 kinase activity or medicated by cytokines produced by p38 kinase activity.

A further aspect of the invention provides the use of a compound of formula (I), or a pharmaceutically acceptable salt or solvate thereof, for the preparation of a medicament for the treatment of a condition or disease state selected from rheumatoid arthritis, osteoarthritis, asthma, psoriasis, eczema, allergic rhinitis, allergic conjunctivitis, adult respiratory distress syndrome, chronic pulmonary inflammation, chronic obstructive pulmonary disease, chronic heart failure, silicosis, endotoxemia, toxic shock syndrome, inflammatory bowel disease, tuberculosis, atherosclerosis, neurodegenerative disease, Alzheimer's disease, Parkinson's disease, Huntington's disease, amyotrophic lateral sclerosis, epilepsy, multiple sclerosis, aneurism, stroke, irritable bowel syndrome, muscle degeneration, bone resorption diseases, osteoporosis, diabetes, reperfusion injury, graft vs. host reaction, allograft rejections, sepsia, systemic cachexia, cachexia secondary to infection or malignancy, cachexia secondary to aquired immune deficiency syndrome (AIDS), malaria, leprosy, infectious arthritis, leishmaniasis, Lyme disease, glomerulonephritis, gout, psoriatic arthritis, Reiter's syndrome, traumatic arthritis, rubella arthritis, Crohn's disease, ulcerative colitis, acute synovitis, gouty arthritis, spondylitis, and non articular inflammatory conditions, for example, herniated/ruptured/prolapsed intervertebral disk syndrome, bursitis, tendonitis, tenosynovitis, fibromyalgic syndrome and other inflammatory conditions associated with ligamentous sprain and regional musculoskeletal strain, pain, for example that associated with inflammation and/or trauma, osteopetrosis, restenosis, thrombosis, angiogenesis, and cancer including breast cancer, colon cancer, lung cancer or prostatic cancer.

A further aspect of the invention provides the use of a compound of formula (I), or a pharmaceutically acceptable salt or solvate thereof, for the preparation of a medicament for the treatment of a condition or disease state selected from rheumatoid arthritis, asthma, psoriasis, chronic pulmonary inflammation, chronic obstructive pulmonary disease, chronic heart failure, systemic cachexia, glomerulonephritis, Crohn's disease, neurodegenerative disease, Alzheimer's disease, Parkinson's disease, epilepsy, and cancer including breast cancer, colon cancer, lung cancer and prostatic cancer.

A further aspect of the invention provides the use of a compound of formula (I), or a pharmaceutically acceptable salt or solvate thereof, for the preparation of a medicament for the treatment of a condition or disease state selected from rheumatoid arthritis, asthma, psoriasis, chronic pulmonary inflammation, chronic obstructive pulmonary disease, chronic heart failure, systemic cachexia, glomerulonephritis, Crohn's disease and cancer including breast cancer, colon cancer, lung cancer and prostatic cancer.

A further aspect of the invention provides the use of a compound of formula (I), or a pharmaceutically acceptable salt or solvate thereof, for the preparation of a medicament for the treatment of a condition or disease state selected from rheumatoid arthritis, neurodegenerative disease, Alzheimer's disease, Parkinson's disease and epilepsy.

A further aspect of the invention provides the use of a compound of formula (I), or a pharmaceutically acceptable salt or solvate thereof, for the preparation of a medicament for the treatment of any type of pain including chronic pain, rapid onset of analgesis, neuromuscular pain, headache, cancer pain, acute and chronic inflammatory pain associated with osteoarthritis and rheumatoid arthritis, post operative inflammatory pain, neuropathic pain, diabetic neuropathy, trigeminal neuralgia, post-hepatic neuralgia, inflammatory neuropathies and migraine pain.

The compounds of formula (I) and their salts, solvates and physiologically functional salts and solvates may be employed alone or in combination with other therapeutic agents for the treatment of the above-mentioned conditions. In particular, in rheumatoid arthritis therapy, combination with other chemotherapeutic or antibody agents in envisaged. Combination therapies according to the present invention thus comprise the administration of at least one compound of formula (I) or a pharmaceutically acceptable salt or solvate thereof and at least one other pharmaceutically active agent. The compound(s) of formula (I) or pharmaceutically acceptable salt(s) or solvate(s) thereof and the other pharmaceutically active agent(s) may be administered together or separately and, when administered separately, this may occur separately or sequentially in any order. The amounts of the compound(s) of formula (I) or pharmaceutically acceptable salt(s) or solvant(s) thereof and the other pharmaceutically active agent(s) and the relative timings of administration will be selected in order to achieve the desired combined therapeutic effect. Examples of other pharmaceutically active agents which may be employed in combination with compounds of formula (I) and their salts and solvates for rheumatoid arthritis therapy include: immunosuppresants such as amtolmetin guacil, mizoribine and rimexolone; anti-TNFα agents such as etanercept, infliximab, diacerein; tyrosine kinase inhibitors such as leflunomide; kalikrein antagonists such as subreum; interleukin 11 agonists such as oprelvekin; interferon beta 1 agonists; hyaluronic acid agonists such as NRD-101 (Aventis); interleukin 1 receptor antagonists such as anakinra; CD8 antagonists such as amiprilose hydrochloride; beta amytoid precursor protein antagonists such as reumacon; matrix metalloprotease inhibitors such as cipemastat and other disease modifying anti-rheumatic drugs (DMARDs) such as methotrexate, sulphasalazine, cyclosporin A, hydroxychoroquine, auranofin, aurothioglucose, gold sodium thiomalate and penicillamine.

EXAMPLES

The following examples are illustrative embodiments of the invention, not limiting the scope of the invention in any way. Reagents are commercially available or are prepared according to procedures in the literature.

LCMS was conducted on a column (3.3 cm×4.6 mm ID, 3 um ABZ+PLUS), at a Flow Rate of 3 ml/min, Injection Volume of 5 μl, at room temperature and UV Detection Range at 215 to 330 nm.

Example 1

N-(4'-{[(3-Methoxybenzyl)amino]carbonyl}-6-methyl-1,1'-biphenyl-3-yl)-2-pyrrolidin-1-ylisonicotinamide a) 2'-Methyl-5'-[(2-pyrrolidin-1-ylisonicotinoyl)amino]-1,1'-biphenyl-4-carboxylic acid (40 mg, 0.1 mmol), HATU (38 mg, 0.1 mmol), HOBT (13 mg, 0.1 mmol), DIPEA (52 μl), and 3-methoxybenzlamine (16.5 mg, 0.12 mmol) were mixed in DMF (1 ml) and stirred at room temperature for 18 h. The solvent was evaporated under vacuum and the residue partitioned between DCM (5 ml) and aqueous sodium carbonate (1M, 5 ml). The organic phase was applied to a silica gel flash column and eluted with toluene/methanol (95:5), which after evaporation of the solvents under vacuum gave N-(4'-{[(3-methoxybenzyl)amino]carbonyl}-6-methyl-1,1'-biphenyl-3-yl)-2-pyrrolidin-1-ylisonicotinamide (21 mg, 40%).

NMR; δH [$^2$H$_6$]—DMSO 10.28, (1H, s), 9.09, (1H, t), 8.19, (1H, d), 7.97, (2H, d), 7.71, (1H, d), 7.66, (1H, s), 7.46, (2H, d), 7.30, (1H, d), 7.24, (1H, t), 6.96–6.80, (5H, m), 4.47, (2H, d), 3.73, (3H, s), 3.43, (4H, m), 2.21, (3H, s), 1.95, (4H, m). LCMS: retention time 2.95 min, MH$^+$521.

b) 2'-Methyl-5'-[(2-pyrrolidin-1-ylisonicotinoyl)amino]-1,1'-biphenyl-4-carboxylic acid 5'-[(2-Chloroisonicotinoyl)amino]-2'-methyl-1,1'-biphenyl-4-carboxylic acid (600 mg, 1.64 mmol) and pyrrolidine (0.6 ml) were heated in a sealed tube at 90° C. for 5 h. The excess pyrrolidine was evaporated under vacuum and the residue purified by flash chromatography (silica) eluting with DCM/ethanol/ammonia (20:8:1). The solvents were evaportated under vacuum to give 2'-methyl-5'-[(2-pyrrolidin-1-ylisonicotinoyl)amino]-1,1'-biphenyl-4-carboxylic acid (546 mg, 83%).

LCMS: retention time 2.74 min, MH$^+$402.

c) 5'-[(2-Chloroisonicotinoyl)amino]-2'-methyl-1,1'-biphenyl-4-carboxylic acid

Methyl 5'-[(2-chloroisonicotinoyl)amino]-2'-methyl-1,1'-biphenyl-4-carboxylate (1.63 g, 4.28 mmol) and lithium hydroxide monohydrate (376 mg, 9.0 mmol) were mixed in water (5 ml) and THF (10 ml) and stirred at room temperature for 90 h. The pH was adjusted to pH3 by addition of hydrochloric acid (2N) and the mixture extracted with ethyl acetate (3×50 ml). The combined extracts were washed with water (75 ml), brine (75 ml), dried (magnesium sulphate) and concentrated under vacuum. The residue was purified by flash column chromatography on silica eluting with DCM/ethanol/ammonia (30:8:1 then 20:8:1). The solvents were evaporated under vacuum to give 5'-[(2-chloroisonicotinoyl)amino]-2'-methyl-1,1'-biphenyl-4-carboxylic acid (1.15 g, 73%).

LCMS: retention time 3.53 min, MH$^+$367.

d) Methyl 5'-[(2-chloroisonicotinoyl)amino]-2'-methyl-1,1'-biphenyl-4-carboxylate 2-Chloropyridine-4-carbonyl chloride (1.58 g, 9.0 mmol) in DCM (10 ml) was added dropwise to a solution of methyl 5'-amino-2'-methyl-1,1'-biphenyl-4-carboxylate (1.81 g, 7.5 mmol) and triethylamine (3.13 ml, 22.5 mmol) in DCM (10 ml) at 0° C. The reaction was stirred at room temperature for 20 h, the solvent evaporated under vacuum and the residue partitioned between ethyl acetate (50 ml) and saturated aqueous sodium bicarbonate (50 ml). The aqueous was extracted with ethyl acetate (50 ml) and the combined organic phases washed with brine (50 ml), dried (magnesium sulphate) and the solvent evaporated under vacuum. The residue was purified by flash column chromatography on silica eluting with DCM/ethanol/ammonia (300:8:1). The solvents were evaporated under vacuum to give methyl 5'-[(2-chloroisonicotinoyl)amino]-2'-methyl-1,1'-biphenyl-4-carboxylate (1.73 g, 61%).

LCMS: retention time 3.69 min, MH$^+$381.

e) Methyl 5'-amino-2'-methyl-1,1'-biphenyl-4-carboxylate

3-Bromo-4-methylaniline (744 mg, 4.0 mmol), (4-methoxycarbonylphenyl)boronic acid (864 mg, 4.8 mmol), tetrakis(triphenylphosphine)palladium (100 mg, 0.087 mmol) and caesium carbonate (2.4 g, 7.37 mmol) were mixed in DME (30 ml) and heated at 90° C. for 20 h. The reaction was absorbed onto silica applied to a silica SPE (10 g) and eluted with ethyl acetate/cyclohexane (0–100% ethyl acetate). The solvent was evaporated from the product fractions under vacuum to give methyl 5'-amino-2'-methyl-1,1'-biphenyl-4-carboxylate (500 mg, 43%).

NMR; δH CDCl$_3$ 8.07, (2H, d), 7.38, (2H, d), 7.07, (1H, d), 6.67, (1H, dd), 6.60, (1H, d), 3.94, (3H, s), 2.14, (3H, s).

Example 2

N-{4'-[(4-Methoxyanilino)carbonyl]-6-methyl-1,1'-biphenyl-3-yl}-2-pyrrolidin-1-ylisonicotinamide 2'-Methyl-5'-[(2-pyrrolidin-1-ylisonicotinoyl)amino]-1,1'-biphenyl-4-carboxylic acid (40 mg, 0.1 mmol), HATU (38 mg, 0.1 mmol), HOBT (13 mg, 0.1 mmol), DIPEA (52 μl), and 4-methoxyaniline (15 mg, 0.12 mmol) were mixed in DMF (1 ml) and stirred at room temperature for 18 h. The solvent was evaporated under vacuum and the residue partitioned between DCM (5 ml) and aqueous sodium carbonate (1M, 5 ml). The organic phase was applied to a silica gel flash column and eluted with DCM/ethanol/ammonia (400:8:1 then 300:8:1), which, after evaporation of the solvents under vacuum, gave N-{4'[(4-methoxyanilino)carbonyl]-6-methyl-1,1'-biphenyl-3-yl}-2-pyrrolidin-1-ylisonicotinamide (16 mg, 30%).

NMR; δH [$^2$H$_6$]—DMSO 10.29, (1H, s), 10.19, (1H, s), 8.19, (1H, d), 8.02, (2H, d), 7.73–7.68, (4H, m), 7.50, (2H, d), 7.31, (1H, d), 6.97–6.92, (3H, m), 6.86, (1H, s), 3.74, (3H, s), 3.43, (4H, m), 2.23, (3H, s), 1.95, (4H, m). LCMS: retention time 3.02 min, MH$^+$507.

Example 3

N-(4'-{[(2-Hydroxybenzyl)amino]carbonyl}-6-methyl-1,1'-biphenyl-3-yl)thiophene-3-carboxamide

Example 4

N-(4'-{[(4-Hydroxybenzyl)amino]carbonyl}-6-methyl-1,1'-biphenyl-3-yl)thiophene-3-carboxamide

Example 5

N-(4'-{[(3-Hydroxybenzyl)amino]carbonyl}-6-methyl-1,1'-biphenyl-3-yl)thiophene-3-carboxamide

Example 6

N-(4'-{[(3,5-Dihydroxybenzyl)amino]carbonyl}-6-methyl-1,1'-biphenyl-3-yl)thiophene-3-carboxamide General Method A {3'[(3-Thiphenylcarbonyl)amino]-6'-methyl-1,1'-biphen-4-yl}carboxylic acid (Intermediate 1, 50 mg, 0.148 mmol), HOBT (20 mg, 0.148 mmol), DIPEA (30.7 µl, 0.178 mmol), EDC (34.1 mg, 0.178 mmol) and the amine (0.148 mmol) were stirred in DMF (1 ml) at room temperature for 2 hours. The reaction was diluted with ethyl acetate (50 ml), washed with hydrochloric acid (0.5M, 2×50 ml), aqueous sodium hydrogen carbonate (2×50 ml) and dried (magnesium sulphate). The solution was reduced to dryness under vacuum to give the desired product.

| Compound | Amine | MH$^+$ | Retention time (minutes) |
|---|---|---|---|
| Example 3 | 2-hydroxybenzylamine | 443 | 3.54 |
| Example 4 | 4-hydroxybenzylamine | 443 | 3.31 |
| Example 5 | 3-hydroxybenzylamine | 443 | 3.35 |
| Example 6 | 3,5-dihydroxybenzylamine | 459 | 3.20 |

(a) {3'-[(3-Thiophenylcarbonyl)amino]-6'-methyl-1,1'-biphen-4-yl}carboxylic acid (Intermediate 1)

A solution of lithium hydroxide monoxide monohydrate (541 mg, 12.9 mmol) in water (8 ml) was added to a solution of methyl {3'-](3-thiophenylcarbonyl)amino]-6'-methyl-1,1'-biphen-4-yl}carboxylate (Intermediate 2, 1.37 g, 4.3 mmol) in THF (10 ml). The reaction was refluxed for 4 hours. Solvent was evaporated in vacuo, hydrochloric acid (0.5M, 50 ml) was added and the product was extracted into ethyl acetate (2×50 ml). The solvent was evaporate in vacuo to afford {3'[(3-thiophenylcarbonyl)amino]-6'-methyl-1,1'-biphen-4-yl}carboxylic acid (1.68 g, 98%).

NMR: δH [$^2$H$_6$]—DMSO 13.10, (1H, bs), 8.33, (1H, dd), 8.03, (2H, d), 7.72, (1H, dd), 7.68–7.60, (3H, m) 7.50, (2H, d), 7.30, (1H, d), 2.20, (3H, s). LCMS: MH$^+$ 338, retention time 3.47 minutes.

(b) Methyl {3'-[(3-thiophenylcarbonyl)amino]-6'-methyl-1,1'-biphen-4-yl}carboxylate (Intermediate 2)

Methyl (3'-amino-6'-methyl-1,1'-biphen-4-yl)carboxylate (1.45 g, 6.0 mmol), thiophene-3-carboxylic acid (0.846 g, 6.6 mmol), HOBT (0.973 g, 7.2 mmol) and 1-(3-dimethylaminopropyl)-3-ethylcarbodiimide hydrochloride (1.38 g, 7.2 mmol) were dissolved in DMF (10 ml). DIPEA (1.26 ml, 7.2 mmol) was added to the stirred solution, which was then stirred for 16 hours at 20° C. The solvent was removed in vacuo and the residue dissolved in ethyl acetate. The ethyl acetate solution was washed sequentially with aqueous sodium hydrogen carbonate (80 ml) and hydrochloric acid (0.5M, 80 ml), then dried (magnesium sulphate). The solvent was removed in vacuo and the residue was purified by silica biotage chromatography eluting with 4:1 cyclohexane:ethyl acetate. To give methyl {3'-[(3-thiophenylcarbonyl)amino]-6'-methyl-1,1'-biphen-4-yl}carboxylate (1.78 g, 84%).

NMR: δH [$^2$H$_6$]—DMSO 10.1, (1H, s), 8.33, (1H, m), 8.05, (2H, d), 7.72, (1H, dd), 7.70–7.60, (3H, m) 7.52,(2H, d), 7.30, (1H, d), 3.89, (3H, s), 2.20, (3H, s). LCMS: MH$^+$ 352, retention time 3.64 minutes.

Example 7

N-(4'-{[(3-Methoxybenzyl)amino]carbonyl}-6-methyl-1,1'-biphenyl-3-yl)isoxazole-5-carboxamide {3'-[(5-Isoxazolylycarbonyl)amino]-6'-methyl-1,1'-biphen-4-yl}carboxylic acid (Intermediate 3, 30 mg), 3-methoxybenzylamine (12.8 mg), HATU (35 mg), HOBT (13 mg) and DIPEA (48 µl) in DMF (1 ml) were stirred for 18 hours at room temperature. The reaction was diluted with ethyl acetate (50 ml), washed with hydrochloric acid (0.5M, 2×25 ml), aqueous sodium hydrogen carbonate (2×25 ml), dried (magnesium sulphate) and the solvent evaporated in vacuo. The residue was purified by mass-directed autoprep to give N-(4'-{[(3-methoxybenzyl)amino]carbonyl}-6-methyl-1,1'-biphenyl-3-yl)isoxazole-5-carboxamide.

NMR; δH [$^2$H$_6$]—DMSO 10.76, (1H, s), 9.11, (1H, t), 8.82, (1H, d), 7.98, (2H, d), 7.72, (1H, dd), 7.68, (1H, d), 7.47, (2H, d), 7.33, (1H, d), 7.28–7.23, (2H, m), 6.92, (2H, m), 6.82, (1H, m), 4.49, (2H, d), 3.75, (3H, s), 2.23, (3H, s). LCMS: MH$^+$ 442, retention time, 3.27 minutes.

(a) {3'-[(5-Isoxazolylcarbonyl)amino]-6'-methyl-1,1'-biphen-4-yl}carboxylic acid (Intermediate 3)

Methyl {3'-[(5-isoxazolylcarbonyl)amino]-6'-methyl-1,1'-biphen-4-yl}carboxylate (Intermediate 4, 2.84 g), sulphuric acid (1M, 50 ml) and ethanol (100 ml) were heated at 75° C. for 2 hours. The reaction was concentrated under vacuum and the resulting precipitate filtered off and washed with water. The resulting solid was purified on a flash silica column eluting with an ethyl acetate/cyclohexane gradient (33–66% ethyl acetate. Evaporation of the solvent under vacuum gave [3'-(5-isoxazolylamino)-6'-methyl-1,1'-biphen-4-yl]carboxylic acid.

LCMS: MNH$_4^+$ 340, retention time, 3.11 minutes.

(b) Methyl {3'-[(5-Isoxazolylcarbonyl)amino]-6'-methyl-1,1'-biphen-4-yl}carboxylate (Intermediate 4)

Methyl (3'-amino-6'-methyl-1,1'-biphen-4-yl)carboxylate (2 g), HATU (3.16 g), DIPEA (4.32 ml), 5-isoxazolecarboxylic acid (0.95 g) in DMF (30 ml) and ethyl acetate (50 ml) were stirred at room temperature for 2 hours. The reaction was diluted with ethyl acetate (500 ml), washed with hydrochloric acid (0.5M, 2×200 ml), aqueous sodium hydrogen carbonate (2×200 ml) and dried (magnesium sulphate). The solvent was evaporated in vacuo to give methyl {3'-[(5-isoxazolylcarbonyl)amino]-6'-methyl-1,1'-biphen-4-yl}carboxylate.

LCMS: [M-H]$^-$ 335, retention time 3.17 minutes.

Example 8

N-{6-Methyl-4'-[({4-[(methylsulfonyl)amino]phenyl}amino)-carbonyl]-1,1'-biphenyl-3-yl}isoxazole-5-carboxamide {3'-[(5-Isoxazolylcarbonyl)amino]-6'-methyl-1,1'-biphen-4-yl}carboxylic acid (30 mg), N-(4-aminophenyl)methane sulphonamide (17.4 mg), HATU (35 mg), HOBT (13 mg) and DIPEA (48 μl) in DMF (1 ml) were stirred for 18 hours at room temperature. The reaction was diluted with ethyl acetate (50 ml), washed with hydrochloric acid (0.5M, 2×25 ml), aqueous sodium hydrogen carbonate (2×25 ml), dried (magnesium sulphate) and the solvent evaporated in vacuo. The residue was purified by mass-directed autoprep to give N-{6-methyl-4'[({4-[(methylsulfonyl)amino]phenyl}amino)carbonyl]-1,1'-biphenyl-3-yl}isoxazole-5-carboxamide.

NMR; δH [$^2$H$_6$]—DMSO 10.76, (1H, s), 10.32, (1H, s), 9.60, (1H, s), 8.81, (1H, d), 8.03, (2H, d), 7.76–7.69, (4H, m), 7.52, (2H, d), 7.33, (1H, d), 7.24, (1H, d), 7.20, (2H, d), 2.95, (3H, s), 2.23, (3H, s). LCMS: MH$^+$ 491, retention time, 3.12 minutes.

Example 9

N-(6-Methyl-4'-{[(4-{[(methylsulfonyl)amino]methyl}phenyl)-amino]carbonyl}-1,1'-biphenyl-3-yl)isoxazole-5-carboxamide {3'-[(5-Isoxazolylcarbonyl)amino]-6'-methyl-1,1'-biphen-4-yl}carboxylic acid (30 mg), N-(4-aminobenzyl)methane sulphonamide (18.6 mg), HATU (35 mg), HOBT (13 mg) and DIPEA (48 μl) in DMF (1 ml) were stirred for 18 hours at room temperature. The reaction was diluted with ethyl acetate (50 ml), washed with hydrochloric acid (0.5M, 2×25 ml), aqueous sodium hydrogen carbonate (2×25 ml), dried (magnesium sulphate) and the solvent evaporated in vacuo. The residue was purified by mass-directed autoprep to give N-(6-methyl-4'-{][(4-{](methylsulfonyl)amino]methyl}phenyl)amino]carbonyl}-1,1'-biphenyl-3-yl)isoxazole-5-carboxamide.

NMR; δH [$^2$H$_6$]—DMSO 10.76, (1H, s), 10.33, (1H, s), 8.81, (1H, d), 8.03, (2H, d), 7.77, (2H, d), 7.72–7.70, (2H, m), 7.52, (3H, m), 7.34, (3H, m), 7.24, (1H, d), 4.13, (2H, d), 2.84, (3H, s), 2.24, (3H, s). LCMS: MNH$_4^+$ 522, retention time, 3.10 minutes.

Example 10

N-4'-{[(3-Methoxybenzyl)amino]carbonyl}-6-methyl-1,1'-biphenyl-3-yl)thiophene-3-carboxamide

Example 11

N-{6-Methyl-4'-[({4-](methylsulfonyl)amino]phenyl}amino)carbonyl]-1,1'-biphenyl-3-yl}thiophene-3-carboxamide General Method B {3'-[(3-Thiophenylcarbonyl)amino]-6'-methyl-1,1'-biphen-4-yl}carboxylic acid (40 mg, 0.12 mmol), 1-(3-dimethylaminopropyl)-3-ethylcarbodiimide hydrochloride (27 mg, 0.14 mmol), HOBT (19 mg, 0.14 mmol) and the appropriate amine (0.13 mmol) were dissolved in DMF (5 ml). DIPEA (25 μl, 0.14 mmol) was added to the solution which was then stirred from 16 hours at 20° C. The solvent was removed in vacuo and the residue was redissolved in ethyl acetate and washed with water. The ethyl acetate layer was separated, dried (magnesium), concentrated in vacuo and purified by mass-directed HPLC.

| Compound | Amine | MH$^+$ | Retention time (minutes) |
|---|---|---|---|
| Example 10 | 3-methoxybenzylamine | 457 | 3.54 |
| Example 11 | N-(4-aminophenyl)methane sulphonamide | 506 | 3.28 |

Example 12

N-(4'-[({3-[(Dimethylamino)methyl]benzyl}amino)carbonyl]-6-methyl-1,1'-biphenyl-3-yl}thiophene-3-carboxamide {3'-[(3-Thiophenylcarbonyl)amino]-6'-methyl-1,1'-biphen-4-yl}carboxylic acid (40 mg, 0.12 mmol), 1-(3-dimethylaminopropyl)-3-ethylcarbodiimide hydrochloride (27 mg, 0.14 mmol), HOBT (19 mg, 0.14 mmol) and the 3-(N,N-dimethylaminomethyl)benzylamine (0.13 mmol) were dissoved in DMF (5 ml). DIPEA (25 μl, 0.14 mmol) was added to the solution which was then stirred for 16 hours at 20° C. Solvent was removed in vacuo and the residue was redissolved in ethyl acetate and washed with water, dried (magnesium sulphate) and concentrated in vacuo. The residue was purified by mass-directed HPLC to give N-[4'-[({3-[(dimethylamino)methyl]benzyl}amino)carbonyl]-6-methyl-1,1'-biphenyl-3-yl}thiophene-3-carboxamide.

LC/MS: MH$^+$ 484, retention time 2.61 minutes.

Example 13

N-(4'-{[(3,5-Dihydroxybenzyl)amino]carbonyl}-6-methyl-1,1'-biphenyl-3-yl)-3-furamide

Example 14

N-(4'{[(2-Hydroxybenzyl)amino]carbonyl}-6-methyl-1,1'-biphenyl-3-yl)-3-furmamide

Example 15

N-(4'{[(3-Hydroxybenzyl)amino]carbonyl}-6-methyl-1,1'-biphenyl-3-yl)-3-furamide

General Method C

[3'-(3-Furoylamino)-6'-methyl-1,1'-biphen-4-yl]carboxylic acid (Intermediate 5, 50 mg, 0.148 mmol), HOBT (20 mg, 0.148 mmol), DIPEA (30.7 μl, 0.178 mmol), EDC (34.1 mg, 0.178 mmol) and the amine (0.148 mmol) were stirred in DMF (1 ml) at room temperature for 2 hours. The reaction was diluted with ethyl acetate (50 ml), washed with hydrochloric acid (0.5M, 2×50 ml), aqueous sodium hydrogen carbonate (2×50 ml) and dried (magnesium sulphate). The solution was reduced to dryness under vacuum to give the desired product.

| Compound | Amine | MH⁺ | Retention time (minutes) |
|---|---|---|---|
| Example 13 | 3,5-dihydroxybenzylamine | 443 | 3.09 |
| Example 14 | 2-hydroxybenzylamine | 427 | 3.43 |
| Example 15 | 3-hydroxybenzylamine | 427 | 3.23 |

(a) [3'-(3-Furoylamino)-6'-methyl-1,1'-biphen-4-yl]carboxylic acid (Intermediate 5)

Methyl [3'-(3-furoylamino)-6'-methyl-1,1'-biphen-4-yl]carboxylate (Intermediate 6, 980 mg, 2.9 mmol) and lithium hydroxide monohydrate (256 mg, 6.1 mmol) in THF (12 ml) and water (6 ml) were heated at 75° C. for 18 h. The THF was evaporated under vacuum and the aqueous adjusted to pH3 with hydrochloric acid (1M). The precipitate which formed was filtered off, washed with ether and dried under vacuum to give [3'-(3-furoylamino)-6'-methyl-1,1'-biphen-4-yl]carboxylic acid (720 mg, 77%).

LCMS: retention time 3.33 min, MH⁺322.

(b) Methyl [3'-(3-furoylamino)-6'-methyl-1,1'-biphen-4-yl]carboxylate (Intermediate 6)

3-Furoic acid (557 mg, 4.97 mmol), HATU (1.89 g, 4.97 mmol), HBTU (560 mg, 4.14 mmol), methyl (3'-amino-6'-methyl-1,1'-biphen-4-yl)carboxylate (1.0 g, 4.14 mmol) and DIPEA (2.17 ml, 12.43 mmol) were mixed in DMF (5 ml) and reaction stirred at room temperature for 18 h. The DMF was evaporated under vacuum, the residue partitioned between DCM (50 ml) and aqueous sodium carbonate (1M, 50 ml) and the aqueous extracted with DCM (2×30 ml). The combined organics were washed with brine (75 ml), dried (magnesium sulphate) and concentrated under vacuum. The residue was purified on a silica flash column eluting with DCM/ethanol/ammonia (500:8:1), which after evaporation of the solvents under vacuum gave methyl [3'-(3-furoylamino)-6'-methyl-1,1'-biphen-4-yl]carboxylate (800 mg, 58%).

LCMS: retention time 3.41 min, MH⁺336.

Example 16

N-(6-Methyl-4'-{[(4-{[(methylsulfonyl)amino]methyl}phenyl)amino]-carbonyl}-1,1'-biphenyl-3-yl)-3-furamide To a solution of [3'-(3-furoylamino)-6'-methyl-1,1'-biphen-4-yl]carboxylic acid (75 mg), HATU (89 mg) and HOBT (32 mg) in DMF (2.25 ml) was added DIPEA (0.122 ml) and N-[(4-aminophenyl)methyl]methane sulphonamide (47 mg) and the mixture stirred for 18 hours at room temperature. The reaction was partitioned between ethyl acetate and hydrochloric acid (0.5M, 20 ml), the organic phase washed with hydrochloric acid (0.5M, 20 ml), saturated sodium hydrogen carbonate solution (2×20 ml) and water (2×20 ml), dried (magnesium sulphate) and the solvent evaporated under vacuum to give N-(6-methyl-4'-{[(4-{[(methylsulfonyl)amino]methyl}phenyl)amino]carbonyl}-1,1'-biphenyl-3-yl)-3-furamide (106.5 mg).

NMR; δH [²H₆]—DMSO 10.33, (1H, s), 9.93, (1H, s), 8.36, (1H, s), 8.03, (2H, d), 7.77, (3H, m), 7.68, (1H, dd), 7.63, (1H, d), 7.51, (3H, m), 7.34–7.28, (3H, m), 6.99, (1H, s), 4.13, (2H, d), 2.84, (3H, d), 2.22, (3H, s). LCMS MH⁺ 504, retention time 3.15 minutes.

Example 17

N-{6-Methyl-4'-[({4-[(methylsulfonyl)amino]phenyl}amino)carbonyl]-1,1'-biphenyl-3-yl}-3-furamide To a solution of [3'-(3-furoylamino)-6'-methyl-1,1'-biphen-4-yl]carboxylic acid (75 mg), HATU (89 mg) and HOBT (32 mg) in DMF (2.25 ml) was added DIPEA (0.122 ml) and N-(4-aminophenyl)methane sulphonamide (44 mg) and the mixture stirred for 18 hours at room temperature. The reaction was partitioned between ethyl acetate and hydrochloric acid (0.5M, 20 ml), the organic phase washed with hydrochloric acid (0.5M, 20 ml), saturated sodium hydrogen carbonate solution (2×20 ml) and water (2×20 ml), dried (magnesium sulphate) and the solvent evaporated under vacuum to give N-{6-methyl-4'-[({4-[(methylsulfonyl)amino]phenyl}amino)carbonyl]-1,1'-biphenyl-3-yl}-3-furamide (114.3 mg).

NMR; δH [²H₆]—DMSO 10.31, (1H, s), 9.93, (1H, s), 9.60, (1H, s), 8.35, (1H, s), 8.02, (2H, d0, 7.78–7.74, (3H, m), 7.67, (1H, dd), 7.63, (1H, d), 7.51, (2H, d), 7.29, (1H, d), 7.20, (2H, d), 6.98, (1H, d), 2.95, (3H, s), 2.22, (3H, s). LCMS MH⁺ 490, retention time 3.17 minutes.

| Abbreviations | |
|---|---|
| DCM | Dichloromethane |
| DIPEA | N,N-Diisopropylethylamine |
| DME | Dimethoxyethane |
| DMF | Dimethylformamide |
| DMSO | Dimethylsulphoxide |
| EDC | 1-(3-Dimethylaminopropyl)-3-ethylcarbodiimide hydrochloride |
| HATU | O-(7-Azabenzotriazol-1-yl)-N,N,N',N'-tetramethyluronium hexafluorophosphate |
| HBTU | O-Benzotriazol-1-yl-N,N,N',N'-tetramethyluronium hexafluorophosphate |
| HOBT | 1-Hydroxybenzotriazole hydrate |
| PyBOP | Benzotriazol-1-yl-oxy-tripyrrolidinophosphonium hexafluorophosphate |
| SPE | Solid phase extraction |
| THF | Tetrahydrofuran |

The activity of the compounds of the invention as p38 inhibitors may be demonstrated in the following assays:

p38 Kinase Assay

The peptide substrate used in the p38 assay was biotin-IPTSPITTTYFFFRRR-amide. The p38 and MEK6 proteins were purified to homogeneity from *E. coli* expression systems. The fusion proteins were tagged at the N-terminus with Gluthathione-S-Transferase (GST). The maximum activation was achieved by incubating 20 uL of a reaction mixture of 30 nM MEK6 protein and 120 nM p38 protein in the presence of 1.5 uM peptide and 10 mM $Mg(CH_3CO_2)_2$ in 100 mM HEPES, pH 7.5, added to 15 uL of a mixture of 1.5 uM ATP with 0.08 uCi [g-³³P]ATP, with or without 15 uL of inhibitor in 6% DMSO. The controls were reactions in the presence (negative controls) or absence (positive controls) of 50 mM EDTA. Reactions were allowed to proceed for 60 min at room temperature and quenched with addition of 50 uL of 250 mM EDTA and mixed with 150 uL of Streptavidin SPA beads (Amersham) to 0.5 mg/reaction. The Dynatech Microfluor white U-bottom plates were sealed and the beads were allowed to settle overnight. The plates were counted in a Packard TopCount for 60 seconds. $IC_{50}$ values were obtained by fitting raw data to % I=100*(1−(I−C2)/

(C1–C2)), where I was CPM of background, C1 was positive control, and C2 was negative control.

α P38 Fluorescence Polarisation Method

αP38 was prepared in house. SB4777790-R Ligand was diluted in HEPES containing $MgCl_2$, CHAPS, DTT and DMSO. This was added to blank wells of a Black NUNC 384 well plate. αP38 was added to this ligand mixture then added to the remainder of the 384 well plate containing controls and compounds. The plates were read on an LJL Analyst and Fluorescence Anisotropy used to calculate the compound inhibition.

The application of which this description and claims forms part may be used as a basis for priority in respect of any subsequent application. The claims of such subsequent application may be directed to any feature of combination of features described herein. They may take the form of product, composition, process or use claims and may include, by way of example and without limitation, one or more of the following claims:

The invention claimed is:
1. A compound of formula (I):

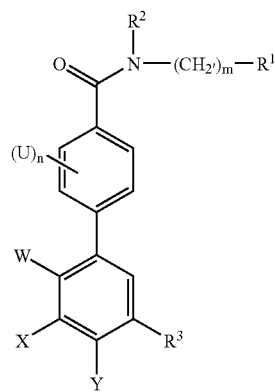

wherein
$R^1$ is a phenyl group which may be optionally substituted;
$R^2$ is selected from hydrogen, $C_{1-6}$alkyl and $-(CH_2)_q-C_{3-7}$cycloalkyl;
$R^3$ is the group $-NH-CO-R^4$;
$R^4$ is selected from hydrogen, $C_{1-6}$alkyl, $C_{1-6}$alkoxy, $-(CH_2)_q-C_{3-7}$cycloalkyl, trifluoromethyl, $-(CH_2)_r-$phenyl optionally substituted by $R^5$ and/or $R^6$, $-(CH_2)_r$heteroaryl optionally substituted by $R^5$ and/or $R^6$, $-(CH_2)_r$heterocyclyl optionally substituted by $R^5$ and/or $R^6$ and $-(CH_2)_r$fused bicyclyl optionally substituted by $R^5$ and/or $R^6$;
$R^5$ is selected from $C_{1-6}$alkyl, $C_{1-6}$alkoxy, $-(CH_2)_q-C_{3-7}$cycloalkyl, $-CONR^7R^8$, $-NHCOR^8$, $-SO_2NHR^7$, $-NHSO_2R^8$, halogen, $-(CH_2)_s$$NR^9R^{10}$, oxy, trifluoromethyl, phenyl optionally substituted by one or more $R^6$ groups and heteroaryl wherein the heteroaryl may be optionally substituted by one or more $R^6$ groups;
$R^6$ is selected from $C_{1-6}$alkyl, $C_{1-6}$alkoxy, halogen, trifluromethyl and $-NR^9R^{10}$;
or $R^5$ and $R^6$, together with the carbon atoms to which they are bound, form a five- or six-membered saturated or unsaturated ring to give a fused bicyclic ring system, wherein the ring that is formed by $R^5$ and $R^6$ may optionally contain one or two heteroatoms selected from oxygen, nitrogen and sulfur;
$R^7$ is selected from hydrogen, $C_{1-6}$alkyl and phenyl wherein the phenyl group may be optionally substituted by one or more $R^6$ groups;
$R^8$ is selected from hydrogen and $C_{1-6}$alkyl;
or $R^7$ and $R^8$, together with the nitrogen atom to which they are bound, form a five- to six-membered heterocyclic ring optionally containing one additional heteroatom selected from oxygen, sulfur and $N-R^x$, wherein the ring may be substituted by up to two $C_{1-6}$alkyl groups;
$R^x$ is selected from hydrogen and methyl;
$R^9$ is selected from hydrogen, $C_{1-6}$alkyl and $-(CH_2)_q-C_{3-7}$cycloalkyl optionally substituted by $C_{1-6}$alkyl;
$R^{10}$ is selected from hydrogen and $C_{1-6}$alkyl;
or $R^9$ and $R^{10}$, together with the nitrogen atom to which they are bound, form a three- to seven-membered heterocyclic ring optionally containing one additional heteroatom selected from oxygen, sulfur and $N-R^x$, wherein the ring may contain up to one double bond and the ring may be substituted by one or more $R^{11}$ groups;
$R^{11}$ is selected from $C_{1-6}$alkyl, oxy, $-CH_2OC_{1-6}$alkyl, trichloromethyl and $-N(C_{1-6}$alkyl$)_2$;
U is selected from methyl and halogen;
W is selected from methyl and chloro;
X and Y are each selected independently from hydrogen, methyl and halogen;
m is selected from 0, 1, 2, 3 and 4, and may be optionally substituted with up to two groups selected independently from $C_{1-6}$alkyl;
n is selected from 0, 1 and 2;
q is selected from 0, 1 and 2;
r is selected from 0 and 1;
s is selected from 1, 1, 2 and 3;
or a pharmaceutically acceptable salt or solvate thereof.

2. A compound according to claim 1 wherein $R^1$ is substituted by one or two substituents selected from halogen, $C_{1-4}$alkyl, trifluoromethyl, $C_{1-4}$alkoxy, benzyloxy, hydroxy, cyano, $-CH_2CH_2OH$, $-(CH_2)_p-NHCH_3$, $-(CH_2)_p-N(CH_3)_2$, $-(CH_2)_pCONR^5R^6$, $-(CH_2)_pCO_2R^5$, $-(CH_2)_pNR^5COR^6$, $-(CH_2)_pOCOR^5$, $-(CH_2)_pOCONR^5R^6$, $-(CH_2)_pNR^5COOR^6$, $-(CH_2)_pCOR^5$, $-(CH_2)_pSO_2NR^5R^6$, $-(CH_2)_pNR^5SO_2R^6$, $-SO_2R^5$, $-(CH_2)_pNR^5R^6$, $-(CH_2)_pNR^5CONR^5R^6$ and $-(CH_2)_pCONR^5SO_2R^6$;
wherein p is selected from 0, 1 and 2; and
$R^5$ and $R^6$ are independently selected from hydrogen, $C_{1-4}$alkyl and phenyl.

3. A compound according to claim 1 wherein group $R^1$ is substituted by one or two substituents selected from $C_{1-4}$alkoxy, hydroxy, $-(CH_2)_pNR^{10}SO_2R^{11}$ and $-(CH_2)_pNR^{10}R^{11}$; and wherein p is selected from 0, 1 and 2.

4. A compound according to claim 1 wherein $R^2$ is selected from hydrogen, $C_{1-4}$alkyl and $-CH_2$-cyclopropyl 5. A compound according to claim 4 wherein $R^2$ is hydrogen.

6. A compound according to claim 1 wherein m is selected from 0, 1 and 2.

7. A compound according to according to claim 1 wherein $R^4$ is selected from $-(CH_2)_r$phenyl optionally substituted by $R^5$ and/or $R^6$ and $-(CH_2)_r$heteroaryl optionally substituted by $R^5$ and/or $R^6$.

8. A compound according to claim 7 wherein $R^4$ is $-(CH_2)_r$heteroaryl optionally substituted by $R^5$ and/or $R^6$.

9. A process for preparing a compound according to claim 1 which comprises:

(a) reacting a compound of formula (IX)

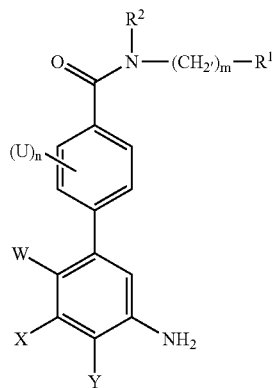

wherein $R^1$, $R^2$, U, W, X, Y, m and n are as defined in claim 1, with a compound of formula (X)

$$R^4CO_2H \qquad (X)$$

wherein $R^4$ is as defined in claim 1, under amide forming conditions, optionally converting the acid compound (X) to an activated form of the acid before reaction with the amine compound (IX); or (b) reacting a compound of formula (XI)

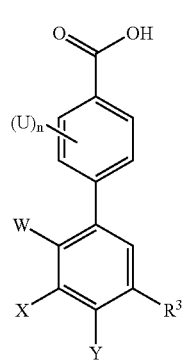

wherein $R^3$, U, W, X, Y and n are defined in claim 1, with a compound of formula (XII)

$$R^1(CH_2)_mNR_2H \qquad (XII)$$

wherein $R^1$, $R^2$ and m are as defined in claim 1, under amide forming conditions.

10. A pharmaceutical composition comprising a compound according to any claim 1 or a pharmaceutically acceptable salt or solvate thereof, in admixture with one of more pharmaceutically acceptable carriers, diluents or excipients.

11. A method for treating a condition or disease state mediated by p38 kinase activity or mediated by cytokines produced by the activity of p38 kinase comprising administrating to a patient in need thereof a compound according to claim 1 or a pharmaceutically acceptable salt or solvate thereof, and wherein the disease or condition mediated by p38 kinase activity or by cytokines produced by the activity of p38 kinase are selected from rheumatoid arthritis, or psoriasis.

12. The compound which is N-(4'{[(3-Methoxybenzyl)amino]carbonyl}-6-methyl-1,1'-biphenyl-3-yl)-2-pyrrolidin-1-ylisonicotinamide; or a pharmaceutically acceptable salt or solvate thereof.

13. The compound according to claim 8 wherein the heteroaryl in $R^4$ is selected from furyl, thienyl, pyrrolyl, oxazolyl, thiazolyl, isoxazolyl, isothiazolyl, imidazolyl, pyrazolyl, oxadiazolyl, triazolyl, tetrazolyl, thiadiazolyl, pyridyl, pyridazinyl, pyrimidinyl, pyrazinyl, and triazinyl.

14. The compound according to claim 13 wherein the heteroaryl is pyridyl, thienyl, oxazolyl, or furyl.

15. The compound according to claim 13 wherein the pyridyl is substituted by $R^6$ and $R^6$ is $NR^9R^{10}$.

16. The compound according to claim 7 wherein r is 0.

17. The compound according to claim 16 wherein n is 0.

18. The compound according to claim 17 wherein X and Y are hydrogen.

19. The compound according to claim 18 wherein W is methyl, $R^2$ is hydrogen, $R^1$ is substituted by one or two substituents selected from $C_{1-4}$alkoxy, hydroxy, —$(CH_2)_p$NR$^{10}$SO$_2$R$^{11}$ and —$(CH_2)_p$NR$^{10}$R$^{11}$; and wherein p is selected from 0, 1 and 2.

20. A compound according to claim 1 which is:
N-(4'-{[(3-Methoxybenzyl)amino]carbonyl}-6-methyl-1,1'-biphenyl-3-yl)-2-pyrrolidin-1-ylisonicotinamide;
N-{4'-[(4-Methoxyanilino)carbonyl]-6-methyl-1,1'-biphenyl-3-yl}-2-pyrrolidin-1-ylisonicotinamide;
N-(4'-{[(2-Hydroxybenzyl)amino]carbonyl}-6-methyl-1,1'-biphenyl-3-yl)thiophene-3-carboxamide;
N-(4'-{[(4-Hydroxybenzyl)amino]carbonyl}-6-methyl-1,1'-biphenyl-3-yl)thiophene-3-carboxamide;
N-(4'-{[(3-Hydroxybenzyl)amino]carbonyl}-6-methyl-1,1'-biphenyl-3-yl)thiophene-3-carboxamide;
N-(4'-{[(3,5-Dihydroxybenzyl)amino]carbonyl}-6-methyl-1,1'-biphenyl-3-yl)thiophene-3-carboxamide;
N-(4'-{[(3-Methoxybenzyl)amino]carbonyl}-6-methyl-1,1'-biphenyl-3-yl)isoxazole-5-caroxamide;
N-{6-Methyl-4'-[({4-[(methylsulfonyl)amino]phenyl}amino)-carbonyl]-1,1'-biphenyl-3-yl}isoxazole-5-caroxamide;
N-(6-Methyl-4'-{[(4-{[(methylsulfonyl)amino]methyl}phenyl)-amino]carbonyl}-1,1'-biphenyl-3-yl)isoxazole-5-carbonoxamide;
N-(4'-{[(3-Methoxybenzyl)amino]carbonyl}-6-methyl-1,1'-biphenyl-3-yl)thiophene-3-carboxamide;
N-{6-Methyl-4'-[({4-[(methylsulfonyl)amino]phenyl}amino)carbonyl]-1,1'-biphenyl-3-yl}thiophene-3-carboxamide;
N-{4'-[({3-[(Dimethylamino)methyl]benzyl}amino)carbonyl]-6-methyl-1,1'-biphenyl-3-yl}thiophene-3-carboxamide;
N-(4'-{[(3,5-Dihydroxybenzyl)amino]carbonyl}-6-methyl-1,1'-biphenyl-3-yl)-3-furamide;
N-(4'-{[(2-Hydroxybenzyl)amino]carbonyl}-6-methyl-1,1'-biphenyl-3-yl)-3-furamide;
N-(4'-{[(3-Hydroxybenzyl)amino]carbonyl}-6-methyl-1,1'-biphenyl-3-yl)-3-furamide;
N-(6-Methyl-4'-{[(4-{[(methylsulfonyl)amino]methyl}phenyl)amino]-carbonyl}-1,1'-biphenyl-3-yl)-3-furamide;
N-{6-Methyl-4'-[({4-[(methylsulfonyl)amino]phenyl}amino)carbonyl]-1,1'-biphenyl-3-yl}-3-furamide; or a pharmaceutically acceptable salt of solvate thereof.

21. A pharmaceutical composition comprising a compound according to claim 20 or a pharmaceutically acceptable salt or solvate thereof, in admixture with one or more pharmaceutically acceptable carriers, diluents or excipients.

* * * * *